(12) United States Patent
Swoyer et al.

(10) Patent No.: US 8,868,210 B2
(45) Date of Patent: Oct. 21, 2014

(54) FIBER OPTIC ASSISTED MEDICAL LEAD

(71) Applicant: Greatbatch Ltd., Clarence, NY (US)

(72) Inventors: John M. Swoyer, Blaine, MN (US); Allison M. Kidder, Boston, MA (US); Jeffrey Zweber, St. Louis Park, MN (US); Scott Brainard, Columbia Heights, MN (US); Valerie Glazier, Eden Prarie, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/038,984

(22) Filed: Sep. 27, 2013

(65) Prior Publication Data

US 2014/0046163 A1  Feb. 13, 2014

Related U.S. Application Data

(60) Continuation of application No. 12/955,417, filed on Nov. 29, 2010, now Pat. No. 8,548,603, which is a division of application No. 11/463,286, filed on Aug. 8, 2006, now Pat. No. 7,844,348.

(60) Provisional application No. 60/595,840, filed on Aug. 9, 2005.

(51) Int. Cl.
*A61N 1/05* (2006.01)
*A61B 5/00* (2006.01)
*A61B 1/00* (2006.01)
*A61B 5/04* (2006.01)

(52) U.S. Cl.
CPC ............ *A61B 5/0084* (2013.01); *A61N 1/0551* (2013.01); *A61N 1/0573* (2013.01); *A61N 1/0587* (2013.01); *A61B 1/00165* (2013.01); *A61B 5/04* (2013.01); *A61N 1/0509* (2013.01); *A61N 1/0558* (2013.01)
USPC .......................................... 607/116; 607/131

(58) Field of Classification Search
CPC ... A61N 1/048; A61N 1/0488; A61N 1/0565; A61N 1/057; A61N 1/0573
See application file for complete search history.

(56) References Cited

U.S. PATENT DOCUMENTS 4,235,246 A  11/1980 Weiss
4,628,943 A  12/1986 Miller
(Continued)

FOREIGN PATENT DOCUMENTS

EP  0149431  7/1985
EP  0795343  9/1997
(Continued)

*Primary Examiner* — Kennedy Schaetzle
*Assistant Examiner* — Erica Lee
(74) *Attorney, Agent, or Firm* — Michael F. Scalise

(57) ABSTRACT

A medical device for placing a medical lead in the human body using minimally invasive techniques is described. One lead includes a lead body connected to a lead head having an aperture for providing fiber optic access to the interior of a helical electrode. The fiber optic shaft may be disposed within or along-side a drive shaft releasably coupled to the lead head to rotate the head. The drive shaft and lead body may be delivered using a delivery catheter. The delivery catheter can be advanced though a small incision to the target tissue site, and the site remotely visualized through the fiber optic scope extending through the lead head aperture. The lead head can be rotated, rotating the helical electrode into the tissue, and the catheter, drive shaft, and fiber optic probe removed.

22 Claims, 15 Drawing Sheets

(56) References Cited

U.S. PATENT DOCUMENTS

| | | | |
|---|---|---|---|
| 5,628,775 | A | 5/1997 | Jackson et al. |
| 5,871,532 | A * | 2/1999 | Schroeppel .................. 607/128 |
| 6,038,463 | A | 3/2000 | Laske et al. |
| 6,192,280 | B1 * | 2/2001 | Sommer et al. ............... 607/122 |
| 6,890,295 | B2 | 5/2005 | Michels et al. |
| 7,369,901 | B1 | 5/2008 | Morgan et al. |
| 2002/0095146 | A1 | 7/2002 | Hutchins et al. |
| 2002/0165536 | A1 | 11/2002 | Kelley et al. |
| 2003/0187461 | A1 | 10/2003 | Chin |
| 2003/0212446 | A1 | 11/2003 | Kaplan et al. |
| 2003/0220676 | A1 | 11/2003 | Helland |
| 2004/0088035 | A1 | 5/2004 | Guenst et al. |
| 2004/0138527 | A1 | 7/2004 | Bonner et al. |
| 2004/0138531 | A1 | 7/2004 | Bonner et al. |
| 2004/0204734 | A1 | 10/2004 | Wagner et al. |
| 2004/0215262 | A1 | 10/2004 | Ferek-Petric |
| 2004/0230282 | A1 | 11/2004 | Cates et al. |
| 2005/0004644 | A1 * | 1/2005 | Kelsch et al. .................. 607/131 |
| 2005/0033394 | A1 | 2/2005 | Seifert et al. |
| 2006/0047333 | A1 | 3/2006 | Tockman et al. |
| 2006/0136035 | A1 | 6/2006 | Hermann et al. |
| 2011/0071358 | A1 | 3/2011 | Swoyer et al. |

FOREIGN PATENT DOCUMENTS

| | | |
|---|---|---|
| WO | WO9955412 | 11/1999 |
| WO | WO02087689 | 11/2002 |
| WO | WO2005107851 | 11/2005 |

\* cited by examiner

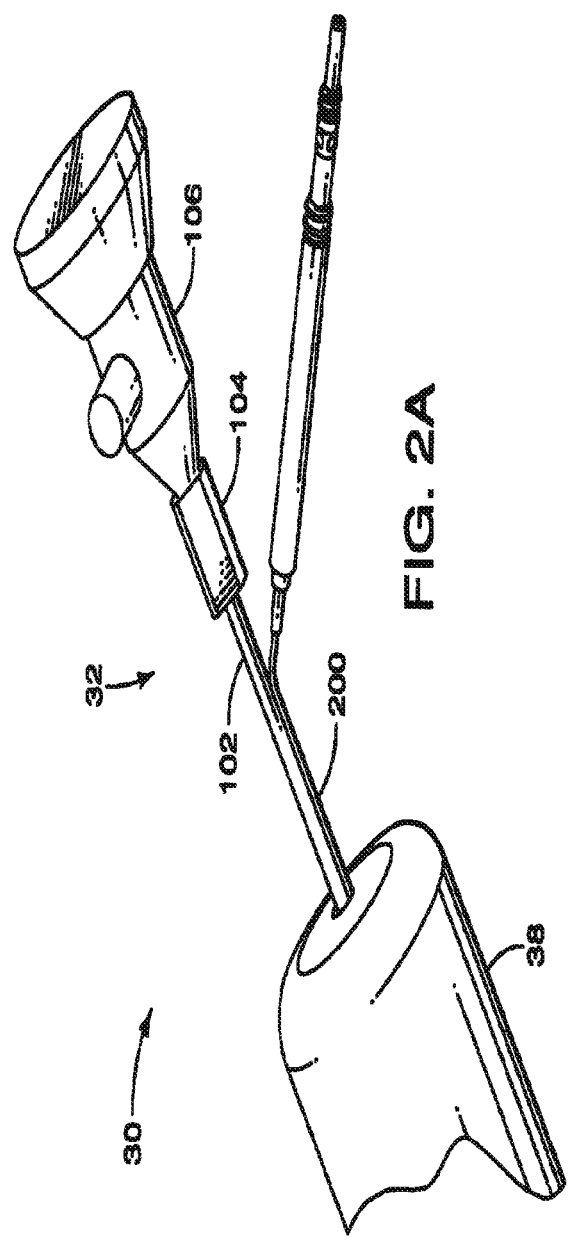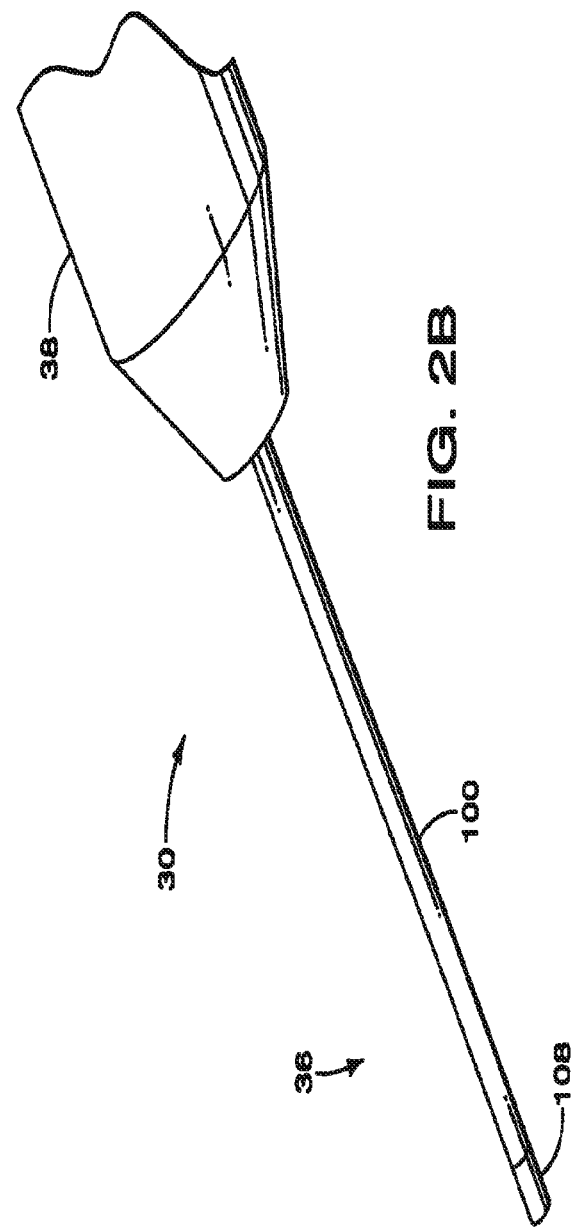

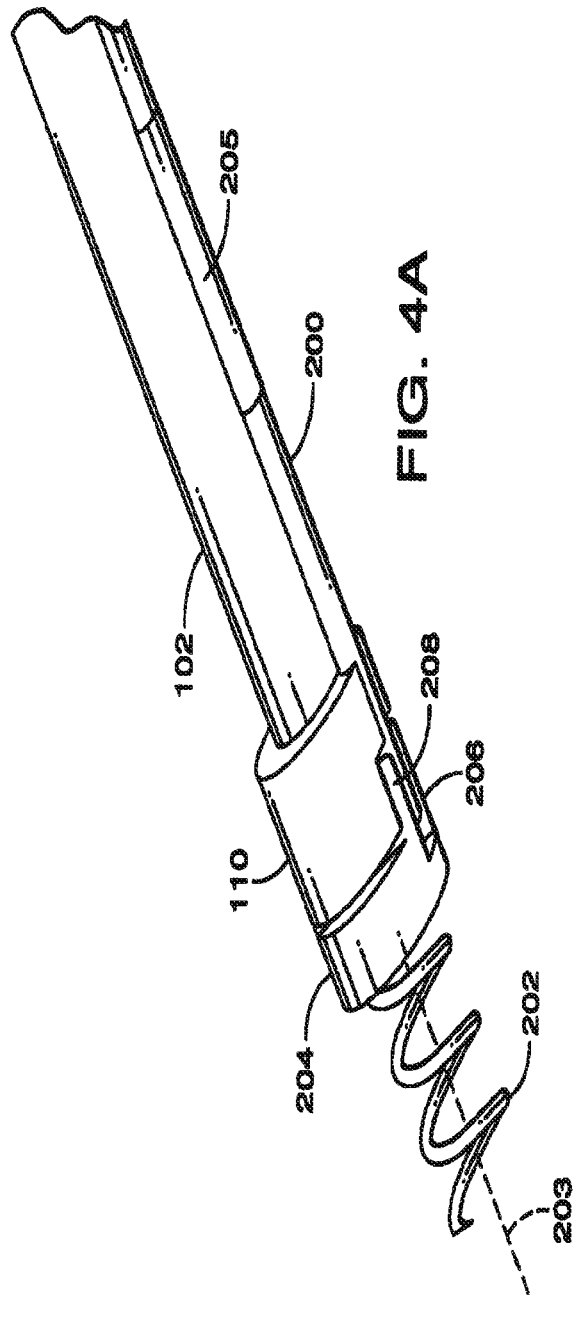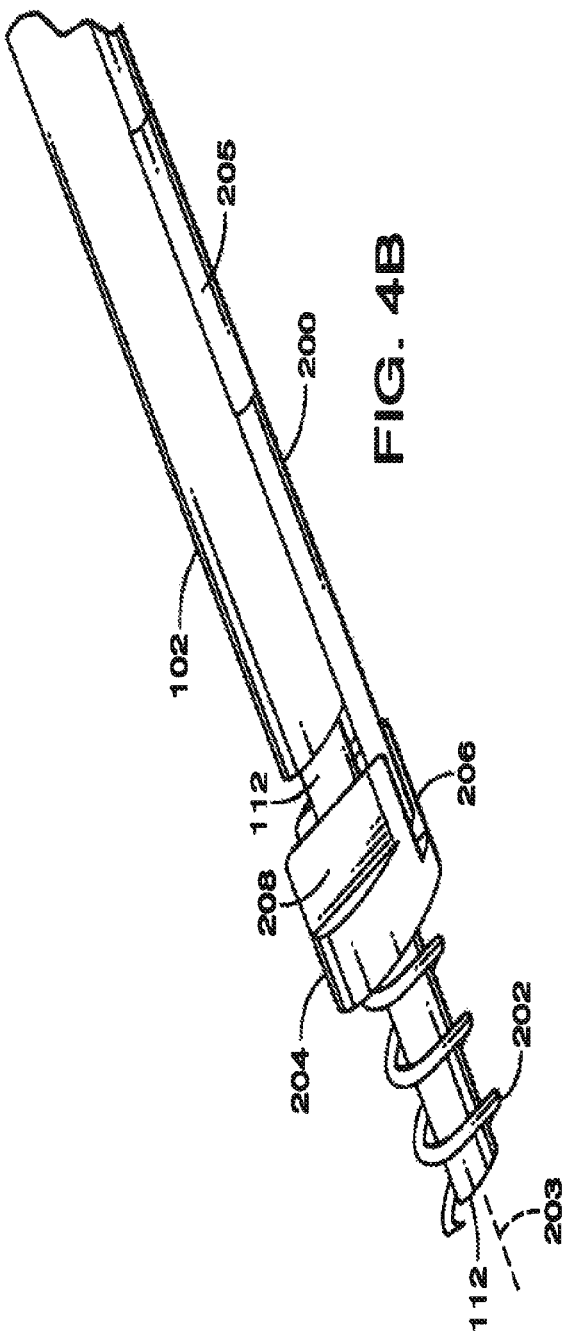

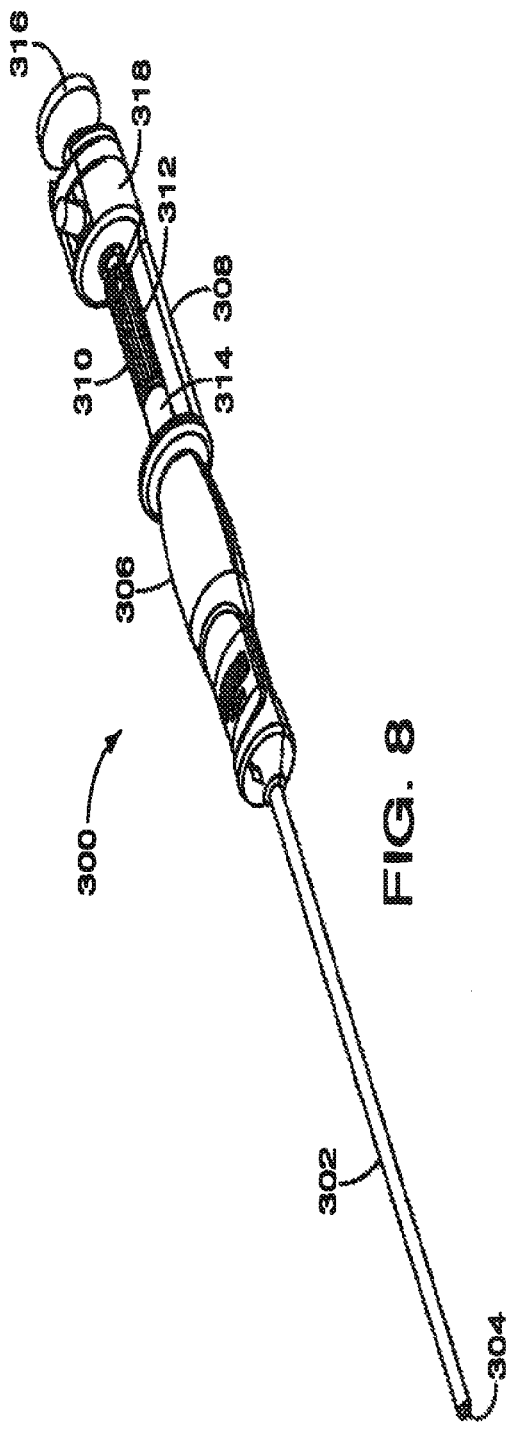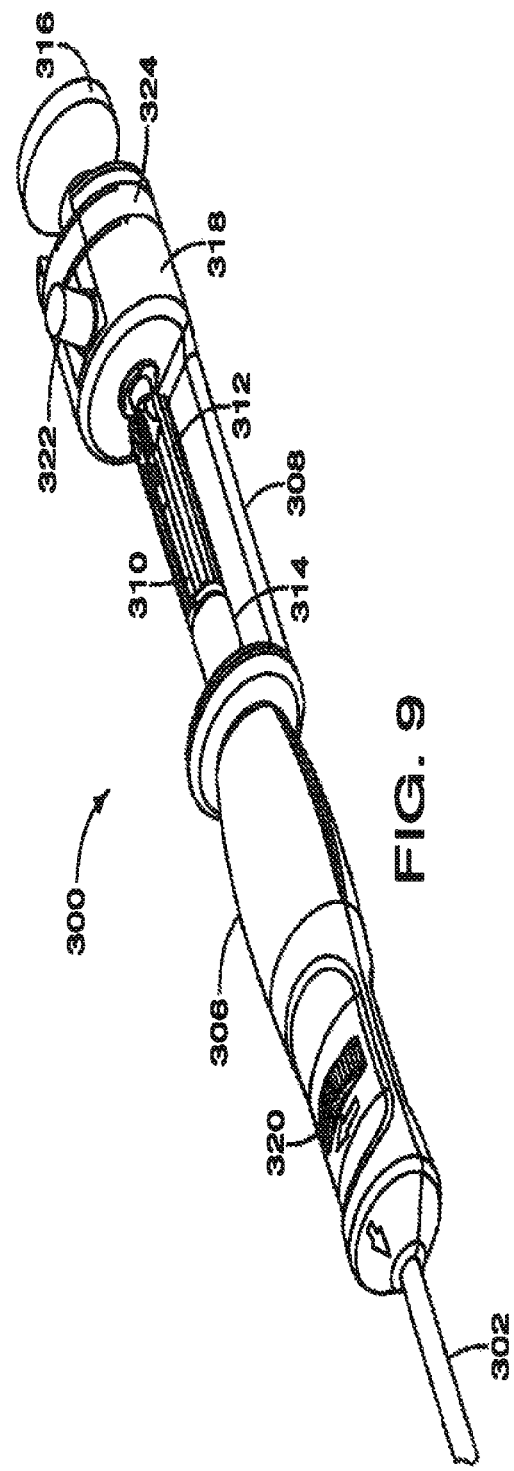

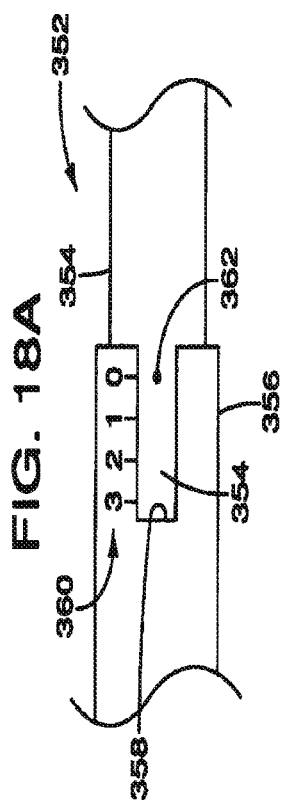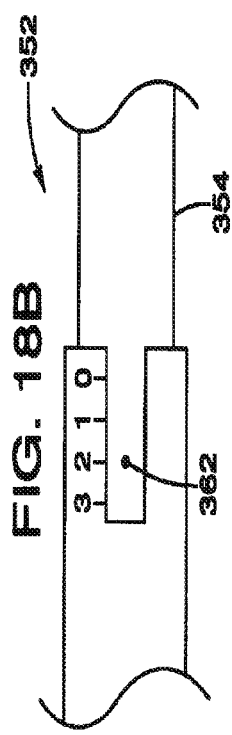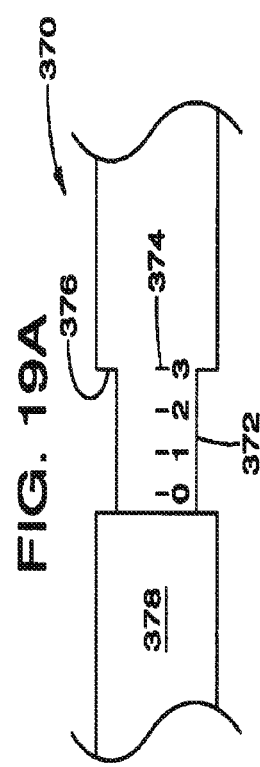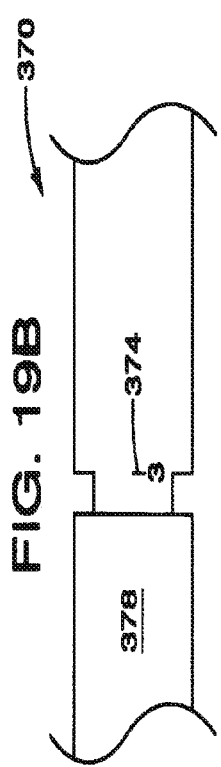

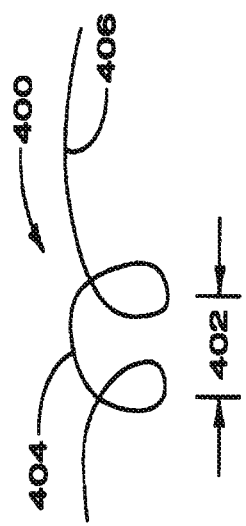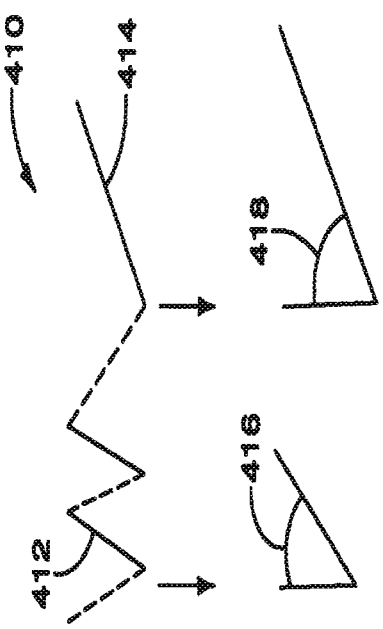

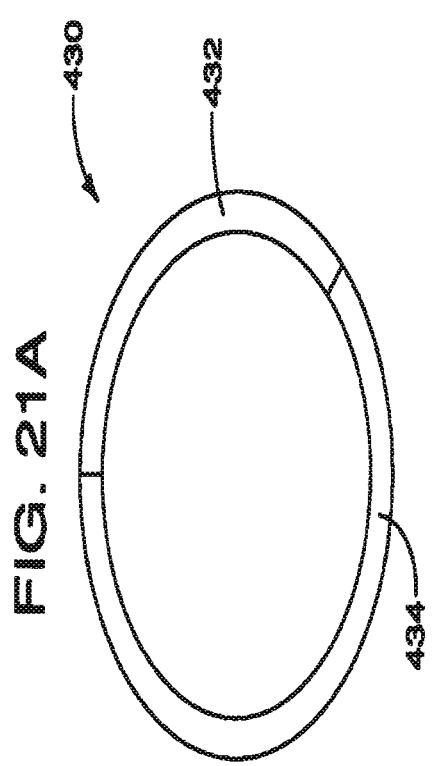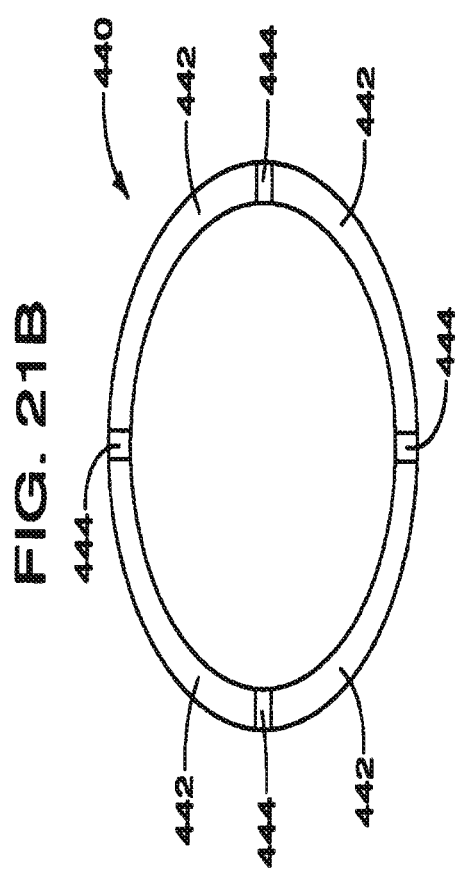

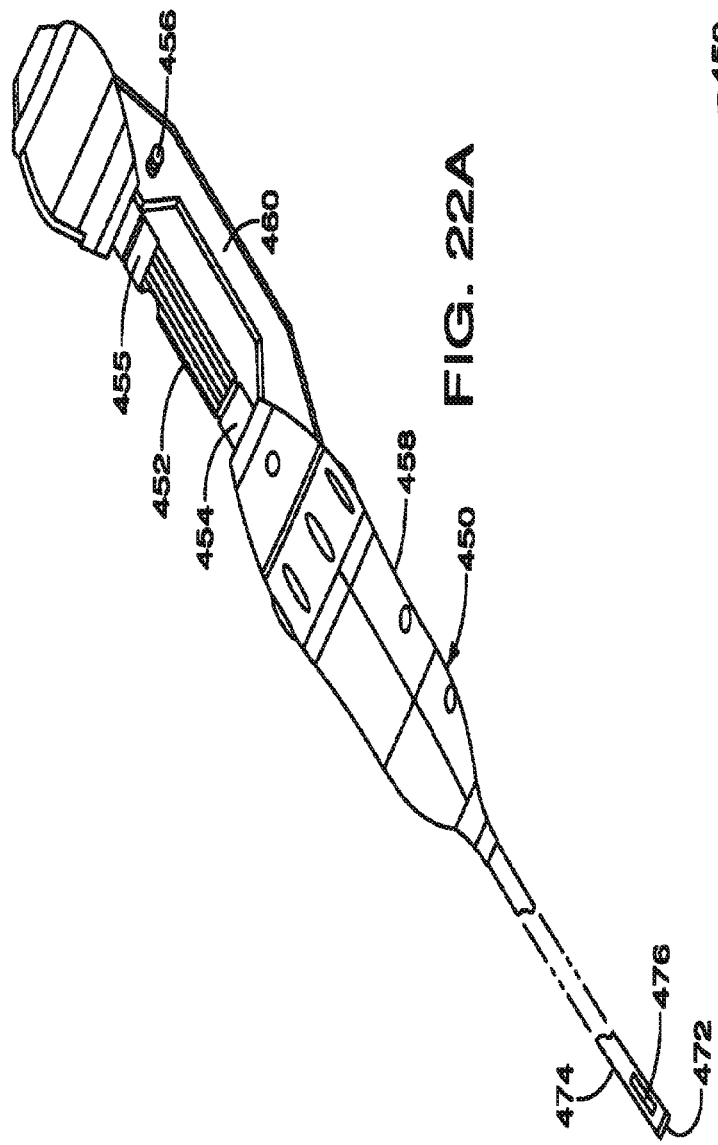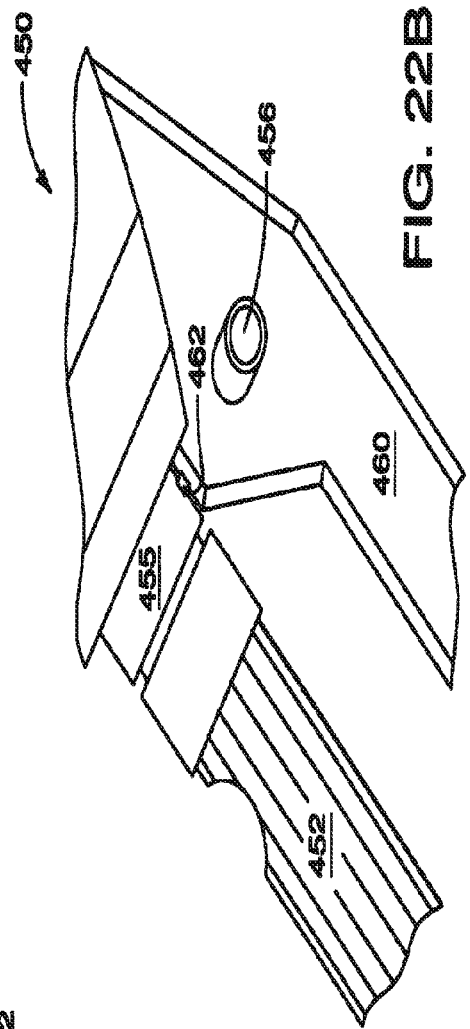

FIBER OPTIC ASSISTED MEDICAL LEAD

RELATED APPLICATIONS

The present application is continuation of U.S. application Ser. No. 12/955,417, filed on Nov. 29, 2010, now U.S. Pat. No. 8,548,603, which is a divisional of U.S. application Ser. No. 11/463,286, filed Aug. 8, 2006, now U.S. Pat. No. 7,844,348, which is a non-provisional of U.S. Provisional Pat. App. Ser. No. 60/595,840, filed Aug. 9, 2005, herein incorporated by reference in its entirety.

FIELD OF INVENTION

The present invention is related to medical devices. More specifically, the present invention includes systems, devices, and methods related to implantable electrical leads which can be positioned using a fiber optic probe. Applications include the visualized placement of epicardial pacing leads, spinal cord stimulation leads, neuro-stimulation leads, HIS bundle leads, gastric stimulation leads, LV apex leads, sensing leads, and others.

BACKGROUND

Several major Cardiac Rhythm Management (CRM) companies have developed special pacemakers "IPGs" that allow for the delivery of resynchronization therapy. This technology uses atrial, synchronized, biventricular pacing and requires placement of a lead in or on the right atrium as well as the right and left ventricles. Placement of a lead inside the left ventricle has not been clinically feasible to date due to dislodgement and the risk of embolism formation potentially leading to a stroke. Placement outside the left ventricle now often includes placing a lead in a convenient location instead of the most efficacious location.

To answer the challenge of placing the left ventricle (LV) lead, considerable effort has gone into the development of special leads and delivery systems for placing the LV lead in a coronary vein. These leads are often referred to as coronary sinus (CS) leads, since the lead passes through the CS. CS leads have been challenging for the electrophysiologist to place and often require considerably more time and increased fluoroscopy exposure than traditional endovascular right side leads. Following implantation, the CS lead may dislodge in 10+% of patients leading to less than desirable performance. At least 10% of the target patients are not candidates for CS leads due to the anatomical structure of their coronary veins.

An alternative to CS leads is the use of epicardial or myocardial leads. Traditionally, these leads have been placed during open chest surgical procedures (sternotomy) or through a less traumatic subxiphiod or subcostal approach to the apex of the heart. The invasiveness of a full sternotomy would not be well tolerated by the CHF patients.

It is generally believed that the target location on the heart for resynchronization therapy is the lateral side of LV 2-3 cm apical of obtuse marginal and circumflex artery junction. Optimization of the target site may be achieved by ECG mapping of the heart to determine the location on the left ventricle that has the latest activation. To reach the target location through MI techniques, endoscopic ports and special endoscopic instruments may be employed. During a minimally invasive procedure it may be desirable to pass the device through a port. The port ID and length limit the amount of curvature that can preexist in some implant tools.

It is desirable for a lead to be implanted with the center axis of the helical electrode normal to the surface of the heart.

Some current epicardial leads and methods require rather large incisions to place the leads. The Fast Tac Flex implant tool (available from Enpath Medical, Minneapolis Minn.) reduces the invasiveness of the procedure, but may be more difficult to use on the posterior side of the heart.

What would be desirable is a device which provides improved minimally invasive access for lead placement on the heart. In particular, what would be advantageous is a device which provides minimally invasive placement of an epicardial lead on the posterior side of the heart. What would especially be advantageous are devices and methods providing visualization and electronic mapping to find the most efficacious lead electrode position to provide optimal patient outcomes.

SUMMARY

The present invention provides an improved implantable medical lead for fixing to tissue in a human body. The lead can include an elongate lead body and an electrical conductor disposed along at least part of the length of the lead body, with a lead head coupled to the lead body near the distal region. The lead can also include one or more electrodes coupled to the head and/or along the lead body to conduct electricity between the electrical conductor and the tissue, with an aperture disposed through the lead head. The aperture can be either closed on all sides or open along a side, depending on the particular embodiment of the invention.

The lead head can have a surface for disposing toward the tissue when fixed, in which the aperture is aligned substantially orthogonally with respect to the lead head surface, such that a shaft inserted through the aperture while the lead head surface is disposed toward the tissue can contact the tissue. The lead electrode may have a central axis, where the aperture has a central axis disposed substantially parallel to the electrode central axis. In some leads the lead head has a longitudinal central axis that is substantially coaxially aligned with the electrode longitudinal central axis. The electrode can be a helical electrode having an interior, where the aperture provides access to the helix interior through the lead head. An elongate fiber optic shaft configured to be received into or through the aperture can also be included with some leads.

The present invention can also provide a system which includes the lead, and can also include a drive shaft, also referred to as a first shaft, disposed along at least part of the length of the electrode body, where the drive shaft is operably coupled to the helical electrode, such that rotating the drive shaft either directly or indirectly rotates the helical electrode. The system can also include a fiber optic shaft disposed along at least part of the length of the lead body, sized to be received into or even through the lead head aperture. In some systems, the drive shaft has one or more lumens therethrough, and the fiber optic shaft is placed within one of the lumens. In other systems, the drive shaft is a solid shaft, configured to releasably engage and rotate the lead head at the distal end. Such a solid drive shaft may have the fiber optic shaft disposed alongside.

Some systems also include a delivery tube or delivery catheter having one or more lumens therethrough, in which the drive shaft, lead body, and fiber optic shaft extend through the delivery tube lumen for at least a part of their length. Some systems have the fiber optic shaft slidably disposed within a separate lumen in the delivery tube or fixedly disposed within a wall of the delivery tube. The system can have the fiber optic shaft adapted to be slidably received through the lead head aperture and within the helical electrode. Some systems have the lead body disposed at about a right angle to the lead head tissue contacting surface while the lead is constrained within the delivery tube, where the lead body is disposed at less than about a 45 degree angle to the lead head tissue contacting surface when unconstrained. Some helical electrodes have a central longitudinal axis with the lead body disposed along a line that is substantially parallel with the helical electrode central axis while constrained within the delivery tube. The lead body in this embodiment is disposed along a line that is substantially parallel with the lead head tissue contacting surface when unconstrained and secured to the tissue. In some systems, the lead body is operably coupled to the drive shaft to rotate with and about a drive shaft central longitudinal axis during drive shaft rotation. The lead can pass through or along the drive shaft.

The present invention also provides an implantable medical lead for fixing to tissue in a human body. The lead can include an elongate lead body having a proximal portion, a distal portion, and a length, with an electrical conductor disposed along at least part of the length of the lead body. The lead can also include a lead head disposed near the distal portion of the lead body and operably coupled to the lead body, with an electrode coupled to the head to conduct electricity between the electrical conductor and the tissue.

The present invention also provides a medical device including a flexible, controllably bendable tube having a lumen therethrough, a distal region, and a proximal region. Some devices have an aperture through the distal region sidewall. An image capture device may capture the image from near the delivery tube distal portion. The device also has a delivery tube handle having a distal region and a proximal region, the delivery tube handle distal region operably coupled to the bendable tube, such that the bending of the tube can be controlled from the delivery tube handle. The delivery tube handle can have a drive shaft handle receiving region in communication with the bendable tube lumen. The device may also have an elongate drive shaft sized to be rotatably disposed within the bendable tube between the bendable tube proximal and distal regions, as well as a drive shaft handle operably coupled to the drive shaft proximal region and rotatably coupled to the delivery tube handle drive shaft handle receiving region. Rotating the drive shaft handle rotates the drive shaft within the bendable tube.

The device may also include a fiber optic shaft sized to be disposed in the bendable tube between at least the bendable tube distal region and the drive shaft handle, and a fiber optic viewer coupled to the fiber optic shaft proximal region to view images from the fiber optic shaft distal region. Some devices include an elongate electrical lead having a distal electrode, a proximal connector, an elongate lead body, and an elongate conductor coupled along the lead body between the distal electrode and the proximal connector. In some devices, the drive shaft handle includes at least one constrained path for taking up excess lead length. The constrained path may include a spiral groove path disposed about a portion of the drive shaft handle. In some embodiments, the spiral groove is a depressed path. In some embodiments, the constrained path is formed by raised surface bumps, pegs, or ridges.

Some devices according to the present invention also include a cavity in the drive shaft handle for receiving the electrical lead proximal connector, such that rotating the drive shaft handle rotates the drive shaft and the lead body about the drive shaft. The drive shaft may be a tubular shaft having a drive shaft lumen therethrough, in which the fiber optic shaft is removably disposed within the drive shaft lumen. The fiber optic shaft is fixedly disposed within the drive shaft or within the bendable tube, in various embodiments.

Some devices include a mechanism for indicating the number of rotations of the drive shaft. Devices can include a mechanism for limiting the number of rotations of the drive shaft to a predetermined number of rotations. In some embodiments, the controllably bendable tube handle further includes a locking mechanism having a locked position and an unlocked position, in which rotation of the drive shaft handle is prevented in the locked position, and rotation of the drive shaft handle is allowed in the unlocked position. The advancement of the lead may be prevented in the locked position and allowed in the unlocked position.

In some embodiments, the controllably bendable tube distal region includes at least one sensor for measuring a property and generating a signal indicative of the property, with the sensor selected from the group consisting of temperature sensors, pressure sensors, oxygen sensors, pH sensors, and chemical sensors, and combinations thereof, coupled to an elongate signal conductor for conducting the signal at least to the bendable tube proximal region.

Some devices include a sensor shaft sized to be disposed in the bendable tube between at least the bendable tube distal region and the bendable tube proximal region, the sensor shaft having a distal region and a proximal region. The sensor shaft can have at least one sensor for measuring a property and generating a signal indicative of the property disposed near the sensor shaft distal region, where the sensor is selected from the group consisting of temperature sensors, pressure sensors, oxygen sensors, pH sensors, and chemical sensors, and combinations thereof, as well as an elongate signal conductor for conducting the signal to the sensor shaft proximal region.

The present invention also provides a method for affixing an electrical lead to a tissue surface, the lead having a lead head coupled to a lead body and an electrode coupled to the lead head. The method can include advancing the lead head to the tissue surface and visualizing the tissue surface using a removable fiber optic shaft disposed through the lead head. The electrode can be secured to the tissue surface and the fiber optic shaft removed from the lead head. Removing the fiber optic shaft occurs after securing the electrode in some methods and before in others. In other methods, the fiber optic shaft remains within the delivery tube. The electrode securing may include rotating the electrode, where the electrode is a helical electrode. In some methods, the helical electrode is fixedly coupled to the head, and the helical electrode, which is optimized for tissue engagement, is rotated by rotating the lead body and the lead head. In other methods, a barbed electrode may be secured by advancing the electrode into the tissue.

In some methods, the visualizing includes utilizing a fiber optic shaft disposed through the lead head through an aperture in the lead head opening into an interior portion of the helix. The visualizing can be done immediately outside of the patient's body, or more remotely, for example, at the other end of a television or computer network signal transmission. Some methods include rotating the lead head coupled to the helical electrode by rotating a drive shaft extending along at least part of the lead body. The drive shaft can be coupled to the lead head which is coupled to the electrode. Some drive shafts have a lumen therethrough, and the fiber optic shaft is disposed at least partially within the drive shaft lumen. Advancing the lead head can include advancing the lead head while the lead body is disposed at least partially within a delivery tube. The fiber optic shaft may be at least partially disposed within the delivery tube.

Devices and systems according to the present invention can be used to deliver leads including, but not limited to, the visualized placement of epicardial pacing leads, spinal cord stimulation leads, neuro-stimulation leads, HIS bundle leads, gastric stimulation leads, LV apex leads, sensing leads, and others. The delivery may be performed, as appropriate, through a sub-zyphoid approach, a mini thoracotomy, a thoracoscopic approach, a transvenous puncture, and puncturing the right atrial appendage from within to gain access to the heart pericardium.

DESCRIPTION OF DRAWINGS

FIG. 2A is a fragmentary, perspective view of the proximal portion of the system of FIG. 1, including an eyepiece coupled to the drive shaft for viewing through a fiber optic shaft disposed through the drive shaft.

FIG. 2B is a fragmentary, perspective view of the distal portion of the system of FIG. 1, showing the delivery tube extending from the handle and terminating in a mapping electrode tip.

FIG. 4A is a fragmentary, perspective view of the lead head having a helical electrode and coupled to the lead body and releasably coupled to the drive shaft distal portion.

FIG. 4B is a fragmentary, perspective view of the lead and drive shaft of FIG. 4A, with the lead head engagement member of the drive shaft removed.

FIG. 8 is a perspective view of another device according to the present invention including a delivery sheath with a proximal handle and a proximal handle extension, having a rotatable drive shaft handle coupled to a drive shaft rotatably disposed within the flexible delivery sheath, the drive shaft handle releasably receiving a proximal connector of the lead body, the tubular drive shaft having a fiber optic shaft received within.

FIG. 9 is a fragmentary, perspective view of the device of FIG. 8 including the delivery sheath handle, handle extension, drive shaft handle, lead proximal connector, and a proximal eyepiece coupled to the fiber optic shaft disposed within the tubular drive shaft.

FIGS. 18A and 18B are fragmentary, perspective views of one mechanism for coupling to the drive shaft handling for visually indicating the number of turns the drive shaft has been rotated.

FIGS. 19A and 19B are fragmentary, perspective views of another mechanism for coupling to the drive shaft handle, for visually indicating the number of turns the drive shaft has been rotated.

FIGS. 20A and 20B are fragmentary views of one helical electrode including a distal end having a larger radius of curvature and more pronounced helical angle than the proximal end.

FIGS. 21A and 21B are end views of other terminal mapping electrodes.

FIGS. 22A and 22B are perspective views of another delivery system according to the present invention, having a locking mechanism for preventing advancement and/or rotation of the helical electrode during mapping.

DETAILED DESCRIPTION

Figure 1:
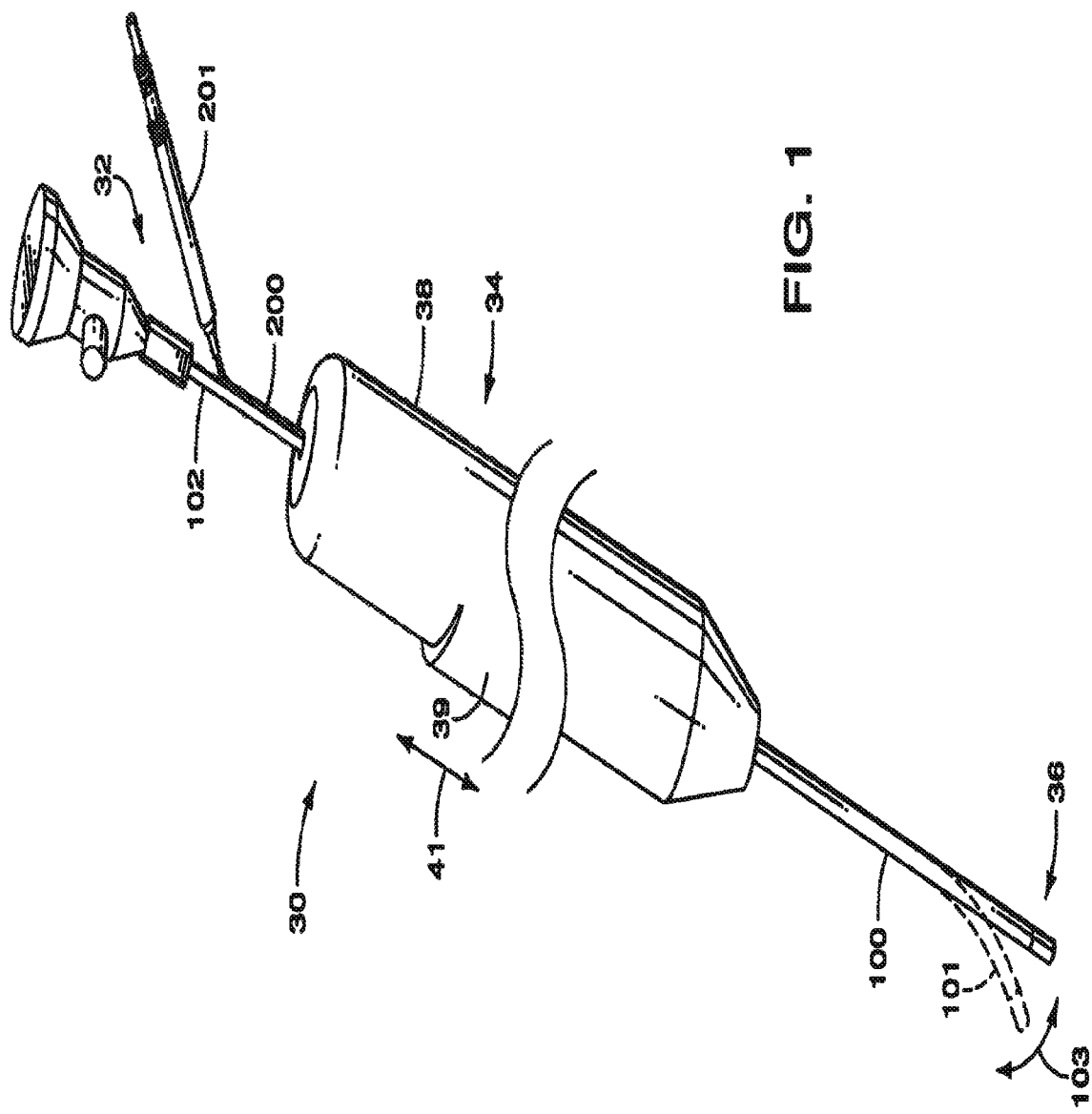
FIG. 1 is a perspective view of a system for placing an epicardial lead, or other electrical lead, including a drive shaft and lead body extending distally into a handle and a delivery catheter containing the drive shaft and lead body extending distally from the handle.

FIG. 1 is a perspective view of a system 30 for delivering an electrical lead using minimally invasive techniques. System 30 includes generally a proximal portion 32, an intermediate portion 34, and a distal portion 36. Proximal portion 32 can include a drive shaft 102, the proximal portion of a lead body 200, and the proximal connector 201 of the lead body. Drive shaft 102 and lead body 200 extend into a handle 38 having a button 39. In some examples of the invention, button 39 can be used to cause the distal end of the delivery tube to curve, allowing the user to steer the device. FIG. 1 illustrates button 39 being slid, as indicated by arrows 41, to cause the delivery tube 100 (discussed below) to curve and bend at the distal end to position 101, as indicated by arrows 103. In other devices, a knob can be rotated to cause the delivery tube to curve. In still other devices, the drive shaft is steerable instead of the delivery tube. Steerable devices, such as steerable guide catheters and guide wires, are well known to those skilled in the art. Steerable devices are discussed in numerous U.S. patents and Patent Publications, including U.S. Patent Publication Nos. 2003/0130598 and 2003/0236493; and U.S. Pat. Nos.

3,605,725; 5,037,391; 5,571,161; 6,171,277; 6,500,130 and 6,530,914, all herein incorporated by reference.

A delivery tube, delivery sheath, or delivery catheter (all used interchangeably) 100 extends distally from handle 38 and terminates in a distal mapping electrode in some embodiments. Drive shaft 102 and lead body 200 can extend side-by-side through the delivery catheter 100. A fiber-optic probe can be slidably inserted through drive shaft 102 to distal portion 36. In some systems, system 30 is about 18 in. long, with handle 38 being about 6 in. long.

The lead body can be made of any suitable material, for example, a polymeric material, such as polyurethane or silicone rubber. The lead body is between about 6 inches and 36 inches long in some devices, and between about 1 and 48 inches long in other devices. The lead head may be cylindrical in some leads, have an outer diameter of between about 1 mm and 32 mm, and a height of between about 1 and 20 mm. The electrode can be of several various electrode types, such as helical, barbed, tined, or sutured. The proximal connector can be used to connect the lead to an implantable or external signal generator, such as a pacemaker, defibrillator, nerve stimulator, or muscle stimulator.

The drive shaft may be made of any suitable material, for example, a polymeric material, such as polyurethane or polyamide (nylon), and can be between about 6 and 36 inches long, or between about 1 and 48 inches long, and between about 1 mm and 20 mm in outer diameter. The drive shaft lumen may be between about 0.5 mm and 3.0 mm, or between about 0.5 and 19 mm in inside diameter, in various embodiments. The delivery catheter can be made of any suitable material, for example, a polymeric material, such as polyurethane or polyamide (nylon), and can have a length of between about 6 and 36 inches, or between about 1 and 48 inches, in various embodiments. The catheter can have an outside diameter of between about 1 mm and 35 mm. The handle can be made of a polymeric material, for example polyamide or ABS, and have an outer diameter of about 25 mm. The fiber optic probe can have a length of between about 6 and 36 inches, or between about 1 and 8 feet, in various embodiments. Fiber optic probes are available from many suppliers, for example, Medivision (Anaheim Calif.).

FIG. 2A shows proximal portion 32 of system 30 in more detail. Drive shaft 102 is coupled to a drive nut 104 which is coupled to eyepiece 106. Drive nut 104 can be used to rotate drive shaft 102 about the fiber-optic shaft within in some embodiments. Some devices rotate eyepiece 106 and the fiber optic shaft along with drive nut 104. Eyepiece 106 can be used for viewing the visual image transmitted through a fiber-optic shaft disposed down drive shaft 102. At the appropriate time, the eyepiece and coupled fiber optic shaft can be withdrawn from drive shaft 102. Lead body 200 and drive shaft 102 may be seen extending into handle 38. When drive shaft 102 is rotated, in some embodiments, lead body 200 rotates with and about drive shaft 102 as the distal end of the lead is rotated into the tissue.

FIG. 2B better illustrates distal portion 36 of system 30. Delivery tube or delivery catheter 100 can be seen extending from handle 38. In the embodiment illustrated, delivery catheter 100 includes a distal mapping electrode tip 108. Mapping electrode 108 can be used to test the electrical properties of the target site prior to implanting the electrode. In some systems, electrode 108 is coupled through a conductor, with the conductor extending through, within, or along, either integral with or separate from, delivery catheter 100, to the proximal end of the device.

Figure 3:
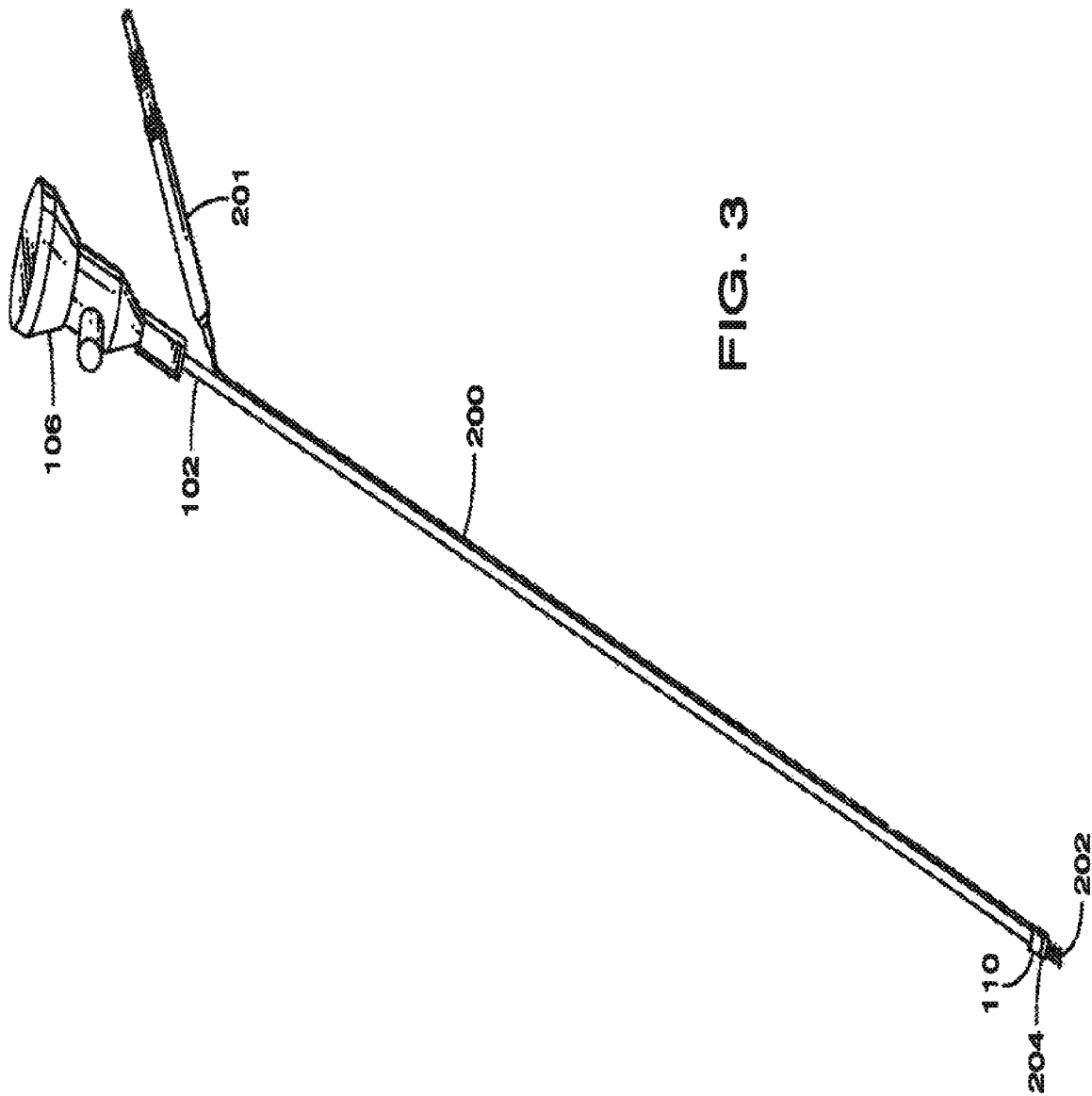
FIG. 3 is a perspective view of the system of FIG. 1, having the handle and delivery catheter removed, showing the lead head releasably coupled to the drive shaft.

FIG. 3 illustrates lead body 200 and drive shaft 102 with the handle and delivery catheter removed. Lead body 200 may be seen to terminate in a lead head 204 coupled to a helical electrode 202. Drive shaft 102 may be seen to terminate in a lead head engagement member or drive element 110. Rotating drive shaft 102 rotates drive element 110 which in turn rotates lead head 204 which also rotates helical electrode 202, in the embodiment shown. In some devices according to the present invention, lead body 200 is fixed in a groove in drive shaft 102. The connector 201 may be secured, for example, with a clip secured to eyepiece 106 and/or drive nut 104 (shown in FIG. 2A).

FIG. 4A shows the distal portion of drive shaft 102 and lead body 200, again with the delivery catheter removed. A second electrode 205 is present in this embodiment, and is coupled to a conductor within lead body 200, Electrode 205 can be a band, coil, or ring extending around lead body 200 in some embodiments. Drive shaft 102 is connected to lead head engagement member or drive element 110. Lead head engagement number 110 is releasably engaged to a protrusion or blade 208 on lead head 204, which carries helical electrode 202. Lead body 200 is coupled to lead head 204 at a point of attachment 206. In the embodiment illustrated, lead head drive member 110 has a cavity or slot which engages lead head protrusion or blade 208. Helix 202 has a central longitudinal axis 203 extending through an interior portion of the helix. In some embodiments, the fiber-optic probe looks down this central longitudinal axis 203 in the interior of helix 202. In other embodiments, the fiber optic probe extends through or into an aperture in the head disposed alongside the electrode. Inspection of FIG. 4A shows that rotating drive shaft 102 will also rotate lead head 204 and helix 202. The releasable attachment of the drive shaft to the lead head can be accomplished using many mechanical designs well known to those skilled in the art. This can include a blade or member in the drive shaft engaging a slot in the lead head, where the blade can be a rectangular blade, a Phillips screwdriver type blade, a Torxs screwdriver type member, a hexagonal Allen wrench type member, etc. The various male and female corresponding members may be reversed as between the lead head and the drive member.

FIG. 4B again shows the distal portion of lead body 200, with the drive element 110 removed and a fiber optic shaft or probe 112 inserted into the interior of helix 202. Blade or protrusion 208 may be better seen in this view. In some embodiments, lead body 200 is molded to lead head 204 at attachment point 206, with the constrained configuration of lead body 200 being substantially parallel to drive shaft 102 as shown in FIG. 4B, such that the attachment point 206 is strained in the configuration shown in this figure, and in which helical central axis 203 will bend away from the central longitudinal axis of drive shaft 102, when not constrained. In some embodiments, helix 202 will, bend about 90° with respect to drive shaft 102 and lead body 200, when unconstrained. In some embodiments, attachment point 206 includes an electrically conductive pivot, which can act to reduce the strain on lead body 200 in the configuration of FIG. 4B, but also allow the lead body to pivot with respect to lead head 204 after delivery and fixation of helix 202 into the target site tissue.

In another embodiment of the invention, sensors, which can be acute monitoring sensors, are disposed near the distal tip of a shaft which is disposed along the same or similar path to that taken by fiber optic shaft 112. As such shafts may resemble shaft 112, a separate drawing in addition to FIG. 4B is not required. The types of sensors could include but are not limited to temperature sensors, pressure sensors, oxygen sensors, pH sensors, chemical sensors, and combinations thereof. There could be more than one sensor at the tip depending on the application. The sensor could also be used with the mapping electrode. The sensor could be delivered through the drive shaft and the aperture in the lead head. Sensors could also be disposed where electrode 205 is located in FIG. 4B. The sensors could generate a signal indicative of the property measured and transmit the signal along or through the shaft, for example using an electrical conductor or a fiber optic conductor. In some embodiments, a fluorescent probe is disposed near a fiber optic shaft tip, which is used to measure one or more properties near the target tissue.

Figure 4C:
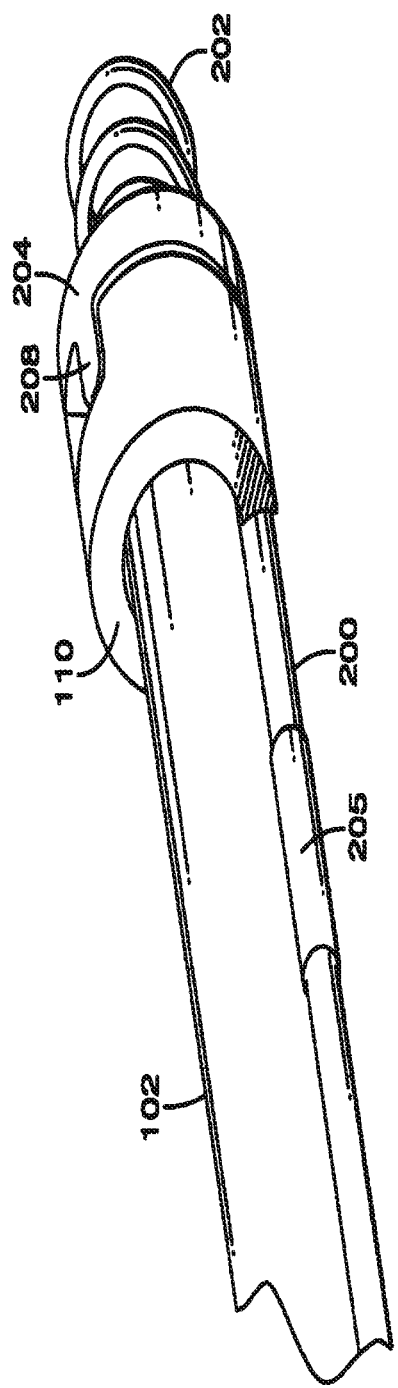
FIG. 4C is a fragmentary, perspective view of the lead and drive shaft of FIG. 4A, showing the lead engagement member coupled to the drive shaft for releasably engaging the lead head.

FIG. 4C illustrates the distal portion of the drive shaft and lead body. Lead body 200 may be seen connecting to lead head 204 which carries helix 202. Drive shaft 102 carries drive element 110 which releasably engages protrusion or blade 208 on lead head 204 to rotate the lead head.

Figure 5:
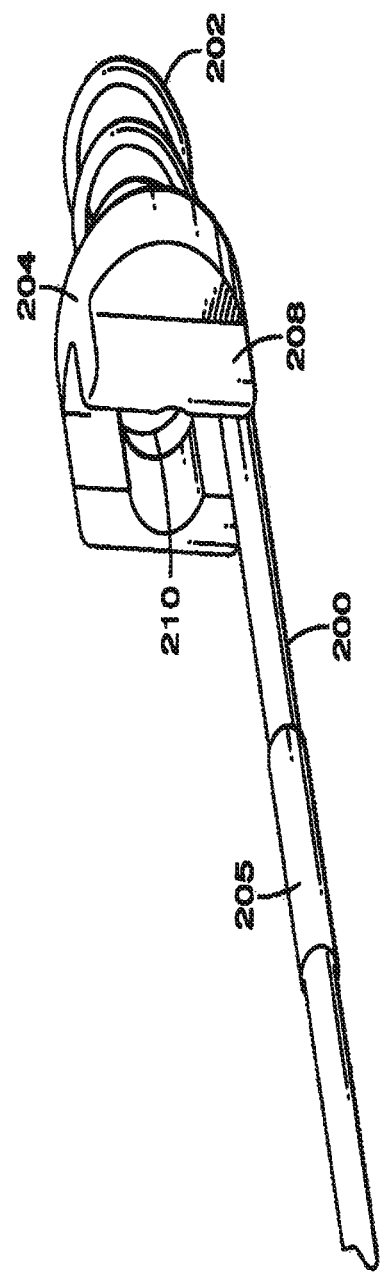
FIG. 5 is a fragmentary, perspective view of a distal portion of the lead of FIG. 4A, showing the aperture through the lead head for receiving a fiber optic probe.

FIG. 5 illustrates lead body 200 coupled to lead head 204. Lead head 204 includes the blade or protrusion 208, helix 202, and also contains an aperture 210 therethrough, Aperture 210 can receive a fiber-optic probe inserted into or through the aperture and also into the interior region of helical coil 202, in some examples of the invention. Second electrode 205 is also shown.

Figure 6:
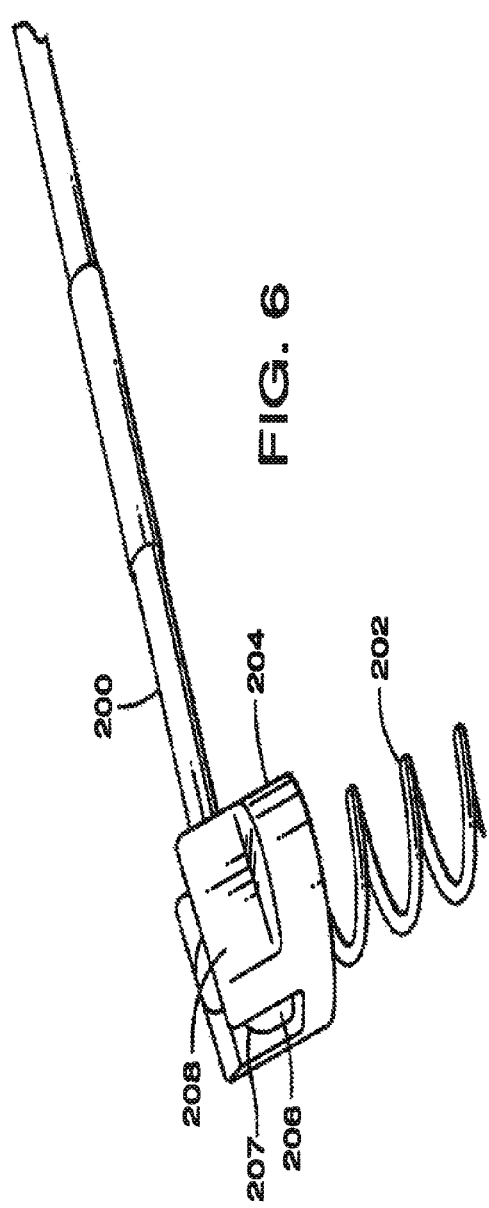
FIG. 6 is a fragmentary, perspective view of the lead of FIG. 5, showing an unconstrained configuration allowing the lead body to be parallel with the tissue surface and the lead head tissue contacting surface, and at right angles to the helical electrode.

FIG. 6 shows lead body 200 coupled to lead head 204 bearing helix 202. An interior slot or cavity 207 may be seen in lead head 204, with slot 207 housing part of lead body 200 within. In this embodiment, lead body 200 is actually configured to be attached at attachment point 206 on the far side of lead head 204 and to lie down partially within slot 207 within lead head 204, which can provide additional strain relief.

Figure 7:
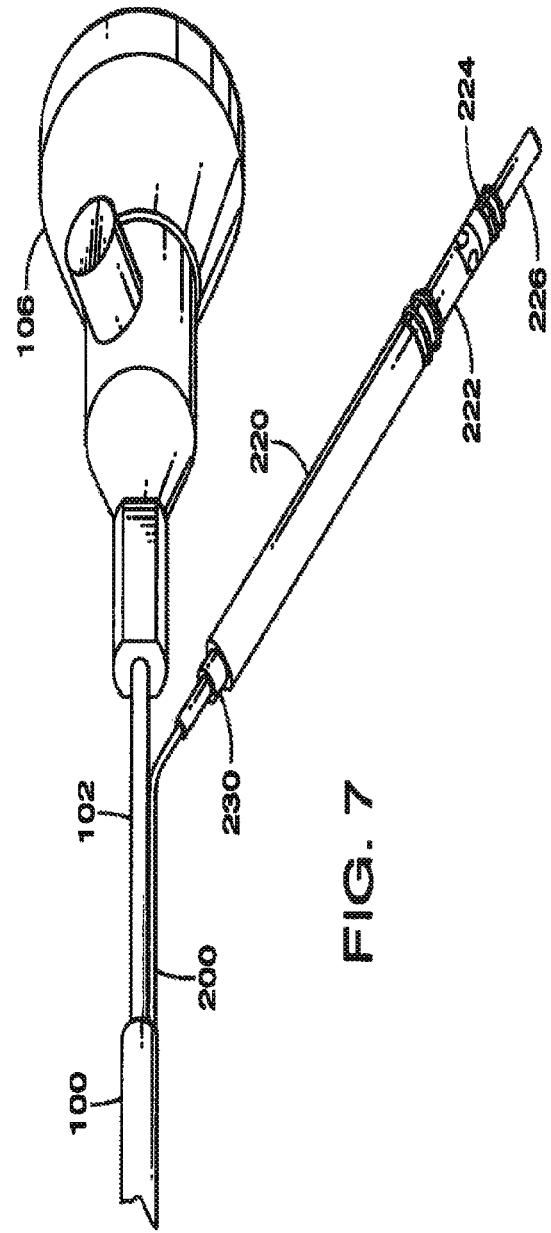
FIG. 7 is a fragmentary, perspective view of the proximal portion of the lead, showing the lead connector.

FIG. 7 illustrates the proximal portion of system 30 previously discussed. An eyepiece 106 is coupled to a fiber optic probe (not shown in FIG. 7) which is disposed within drive shaft 102. Eyepiece 106 and the connected fiber optic shaft can be proximally retracted from within drive shaft 102 at the proper time, for example, after site visualization or lead fixation. Lead body 200 may be seen coupled to a strain relief portion 230. The connector portion of the lead includes generally a connector sleeve 220, a connector ring 222, a seal 224, and a connector pin 226.

FIG. 8 illustrates another device 300 according to the present invention. Device 300 includes a flexible, steerable delivery tube or sheath 302 having a distal mapping ring electrode 304. Flexible sheath 302 is coupled to a control handle 306 having a proximal handle extension 308. A drive shaft (not shown in FIG. 8) is coupled to a proximal drive shaft handle 312 having a bushing 314 rotatably disposed within handle 306. Drive shaft handle 312 includes a cradle for receiving a lead proximal connector 310. Drive shaft handle 312 can be used to rotate both the drive shaft within flexible sheath 302 and the lead body connected to lead proximal connector 310. Lead body proximal connector 310 can be removed from handle 312, while still connected to the lead body. Handle extension 308 includes a receiver 318 for releasably securing a fiber optic eyepiece 316 which is coupled to a fiber optic shaft (not shown in FIG. 8) which can extend down the center of the tubular drive shaft disposed within the flexible sheath 302.

FIG. 9 illustrates the proximal, region of device 300 in more detail. Handle 306 includes a rotatable knob 320 for controllably bending or steering delivery sheath 302. Such control mechanisms are well known to those skilled in the art, and are the subject of several patents and patent applications assigned both to the assignee of the present patent application and others. Such controlled bending mechanisms do not require further discussion here. Handle extension 308 receives bushing 314 coupled to drive handle 312 which houses lead proximal connector 310. Bushing 314 can rotate within handle 306 allowing drive handle 312 to rotatably screw a helical electrode into the target tissue. In some embodiments of the invention, outer spiral grooves are included either in the outside surface of bushing 314 or drive shaft handle 312, allowing a lead body having excess length to be dressed, thereby allowing leads having multiple lengths be delivered with the same device. A lead body (not visible in FIG. 9) is coupled to proximal connector 310 and may lie along the outside of bushing 314 in a groove. Device 300 can include a fiber-optic eyepiece receiver 318 having a locking ring 324. Locking ring 324 can have a C-shape, such that a fiber optic eyepiece 316 can be manually or mechanically advanced or retracted and/or released from the fiber-optic eyepiece receiver 318 by aligning the opening in the C-shape locking ring with the slot visible in the receiver 318. A light admission port 322 is visible, disposed in the slot, allowing light to be shined into the fiber optic shaft extending from the eyepiece 316 down through flexible sheath 302.

Figure 10:
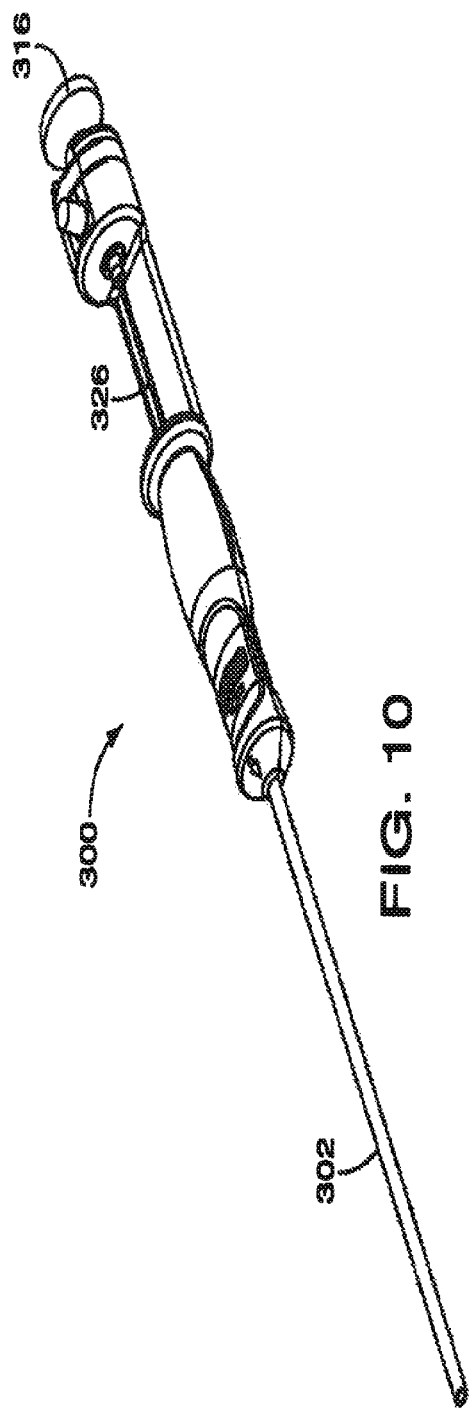
FIG. 10 is another perspective view of the device of FIG. 8, having the drive shaft, drive shaft handle, and lead proximal connector removed, exposing the fiber optic shaft coupled to the eyepiece and extending down the flexible delivery sheath.

FIG. 10 offers another view of device 300, showing a fiber optic shaft 326 coupled to eyepiece 316. In this view, the drive shaft handle and lead have been removed. In some embodiments, fiber optic shaft 326 is disposed within the tubular drive shaft. In such embodiments, the fiber optic shaft may be removed and reused. In other embodiments, fiber optic shaft 326 is disposed within a portion of the flexible delivery sheath 302. In one such embodiment, the fiber optic shaft is slidably disposed within a separate lumen within the flexible sheath wall. In still another embodiment, the fiber optic shaft is fixedly secured within the flexible sheath or drive shaft, cannot be removed easily, and may be intended to serve as a single-use product.

Figure 11:
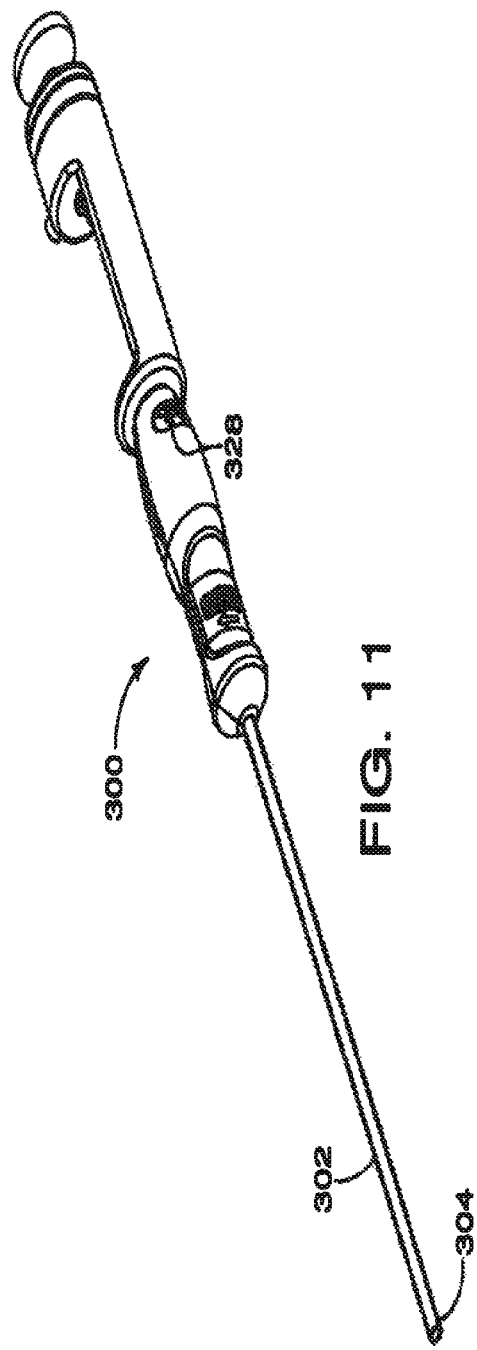
FIG. 11 is another perspective view of the device of FIG. 8, showing the terminal mapping electrode on the delivery sheath and the pin on the underside of the delivery sheath proximal handle which is electrically coupled to the terminal mapping electrode.

FIG. 11 shows the underside of device 300. The underside includes an electrical terminal connector 328 which is electrically coupled to ring mapping electrode 304 in some embodiments. Connector 328 may be referred to as a "PSA" connector. Connector 328 in conjunction with electrode 304 can be used to map the surface of the tissue on which the electrode is to be placed. This can be done by bending sheath 302 and contacting various tissue sites, while monitoring the electrical characteristics through a device coupled to connector 328.

Figure 12:
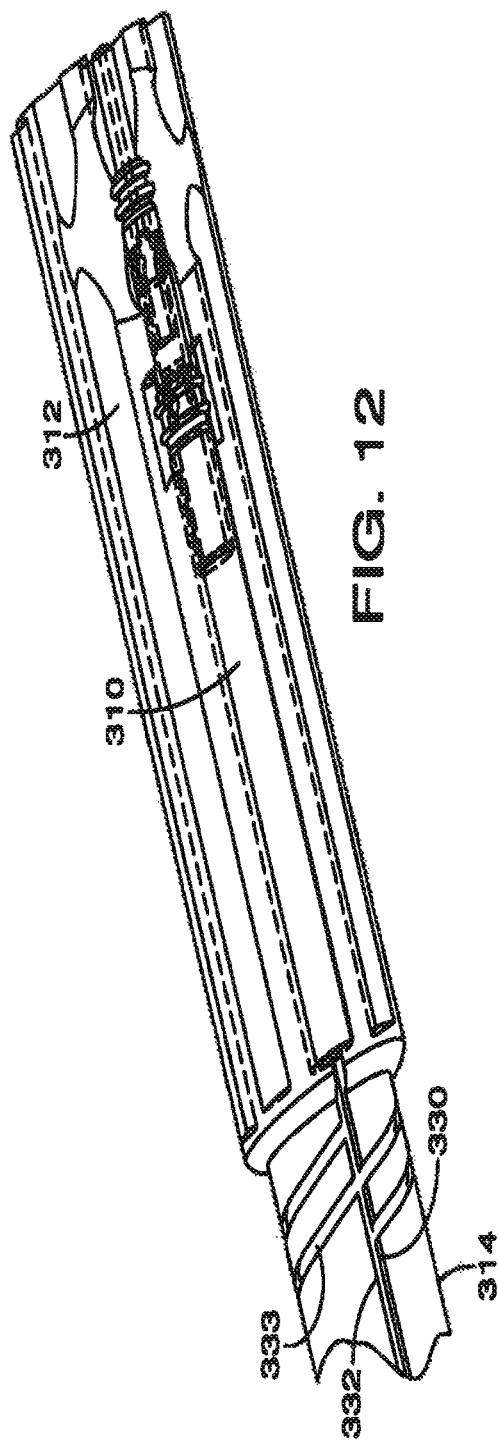
FIG. 12 is a fragmentary, perspective view of the device of FIG. 8, showing the drive shaft handle receiving the lead body proximal connector, with the lead body extending along-side the drive shaft.

FIG. 12 illustrates drive shaft handle 312 having a cradle or receiving area for receiving lead proximal connector 310. Such a connector was previously illustrated in FIG. 3 at reference numeral 201. Proximal connector 310 can be a standard size electrical connector, e.g. 151, well known to those skilled in the art. Handle 312 can include bushing 314 which can be rotatably disposed within the handle. Lead proximal connector 310 is coupled to a lead body 330, which can lie within a groove 332 in bushing 314. As previously discussed, some embodiments can include a spiral outer groove 333 for dressing excess lead length around the bushing in a controllable manner. As is discussed with respect to FIGS. 18A, 18B, 19A, and 19B, bushing 314 may include a rotation indicator and/or counter and/or limiter, in some embodiments.

Figure 13:
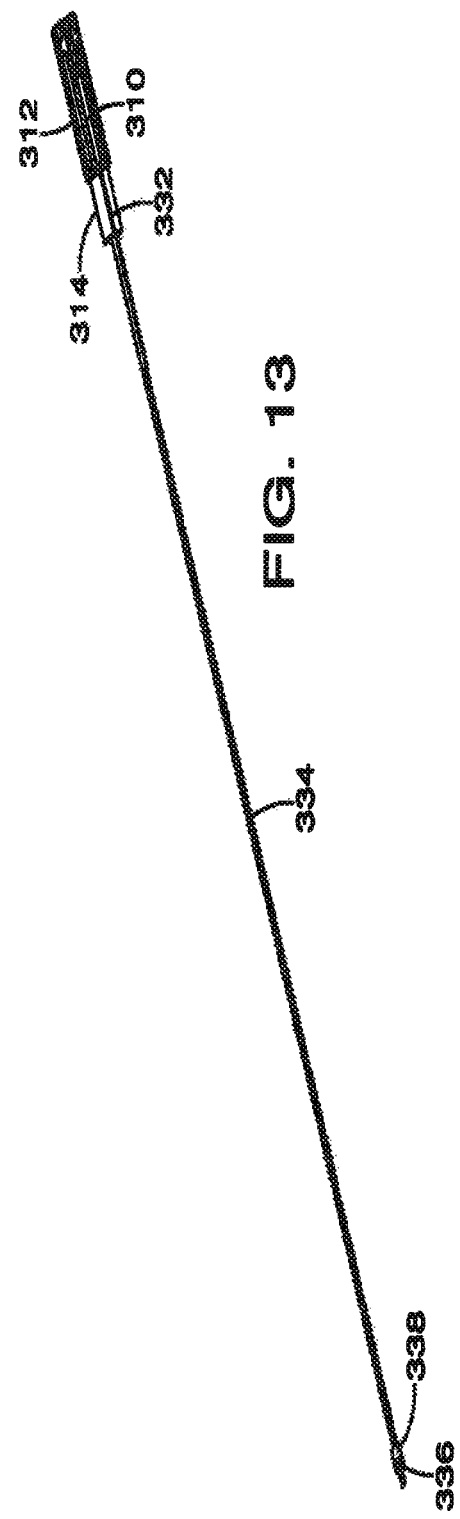
FIG. 13 is a perspective view of the device of FIG. 8, showing the drive shaft extending from the drive shaft handle, the lead body, lead distal electrode, and lead proximal connector.

FIG. 13 shows drive shaft 334 coupled to a lead head engagement member 338 which is engaged to a lead head 336. Lead body 334 is coupled to lead proximal connector 310 which is received within drive shaft proximal handle 312, as previously described. Lead body 334 is dressed in groove 332 formed in bushing 314.

Figure 14:
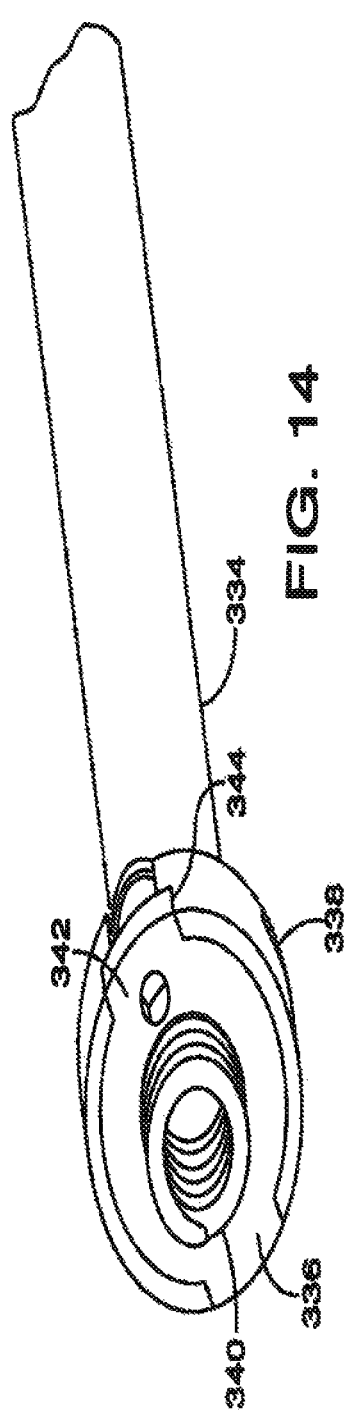
FIG. 14 is a fragmentary, perspective view of the lead distal end including a helical electrode, and a lead head engagement member coupled to the drive shaft.

FIG. 14 shows drive shaft 334 coupled to lead head engagement member 338 which is engaging lead head 336. Lead head 336 includes ears 342 which are engageably received by channels 344 in lead head engagement member 338. Helix electrode 340 may also be seen, having an aperture therethrough which may slidably receive a fiber-optic shaft in some embodiments.

Figure 15:
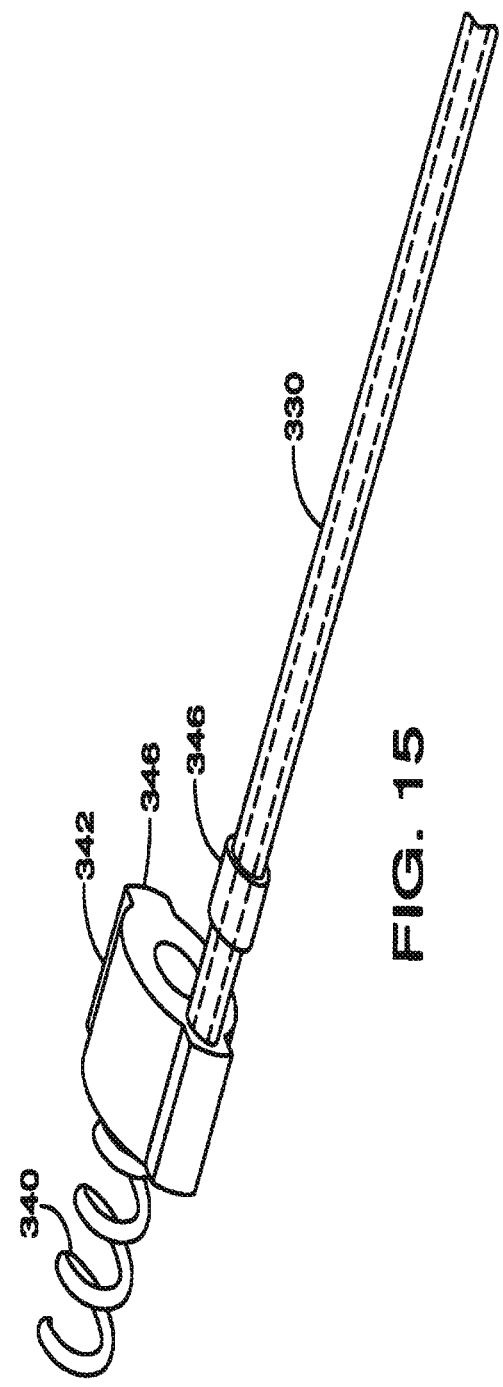
FIG. 15 is a fragmentary, perspective view of the device of FIG. 8, showing the lead body, lead head, and helical electrode.

FIG. 15 shows helix electrode 340 coupled to lead head 342 having ears 346. Lead body 330 may be seen, also carrying a ring electrode 346, which may be present in some embodiments of the invention. In some embodiments, ring electrode 346 may serve as an anode. In FIG. 15, the drive shaft and the fiber optic shaft have been removed to more clearly show the lead distal region.

Figure 16:
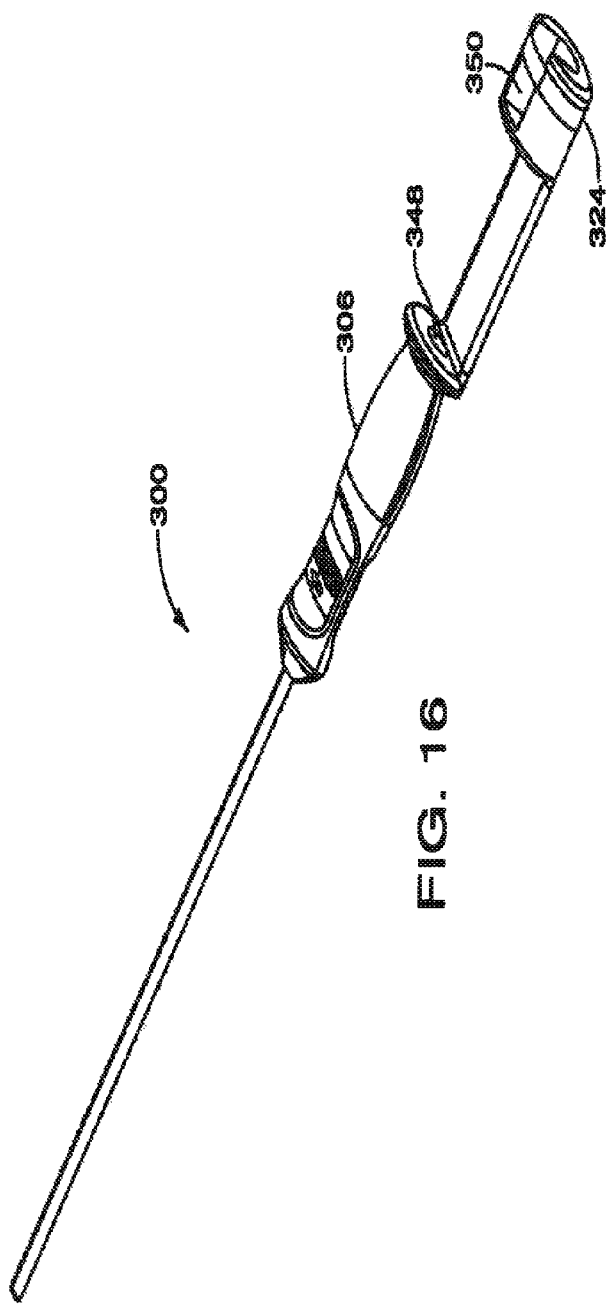
FIG. 16 is a perspective view of the device of FIG. 8, showing the flexible delivery sheath proximal handle and extension including a rotatable locking ring for allowing the locking and releasing of the fiber optic proximal eyepiece.

FIG. 16 shows device 300 from another angle. Handle 306 includes an aperture or internal bearing surface 348 for rotatably receiving the drive shaft bushing, previously described. Locking ring 324 may be seen, in the locking position over fiber-optic eyepiece receiving slot 350.

Figure 17:
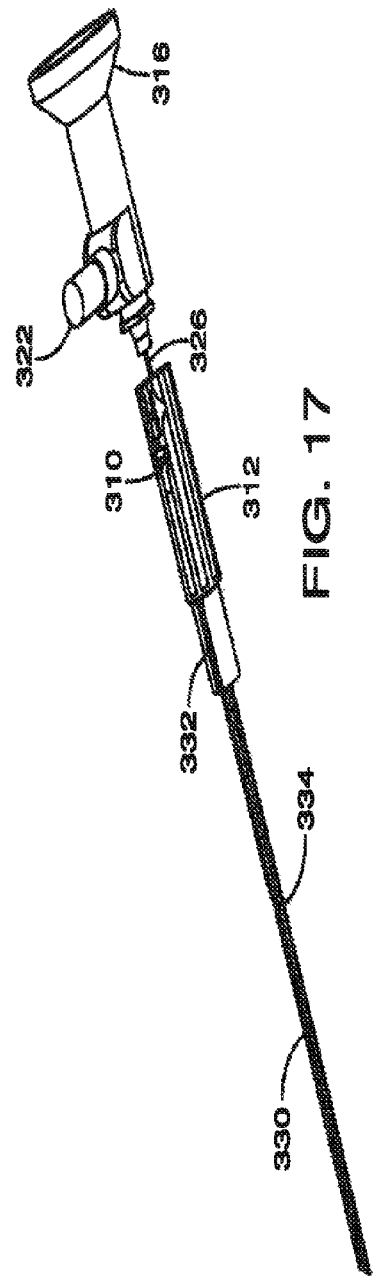
FIG. 17 is another fragmentary, perspective view of the device of FIG. 8, showing the eyepiece coupled to the fiber optic shaft which is disposed within the drive shaft which is disposed along-side the lead body.

FIG. 17 shows eyepiece 316 with light admission port 322 coupled to fiber optic shaft 326. Fiber-optic shaft 326, in this embodiment, is slidably disposed into drive shaft handle 312 and into drive shaft 334. Lead body 330 extends side-by-side along drive shaft 334 in this embodiment. Lead body 330 extends through longitudinal groove 332 and is coupled to proximal lead connector 310.

FIG. 18A illustrates a mechanism 352 for replacing bushing 314 and/or receiving aperture 348, illustrated in FIGS. 9 and 16, respectively. In this new mechanism, bushing (or inner shaft) 354 can be received within tube 356, Bushing 354 is referred to as a bushing for the sake of continuity; even though in various embodiments this part may serve as a threaded member and even have rotation indicating mechanisms incorporated therein. Bushing 354 and tube 356 can be cooperatively threaded to allow the rotation of bushing 354 within tube 356 to also advance bushing 354 longitudinally within tube 356. In this embodiment, a slot 358 within tube 356 allows a portion of bushing 354 to be visible through the slot. A visual marker, dot 362, indicates the longitudinal and rotational progression of bushing 354 within tube 356. Other visual indicia, counting the number of rotations, indicated as numbers zero through three, are shown at 360. As bushing 354 is rotated by the drive shaft handle to drive the drive shaft and the helical electrode into the target tissue, dot 362 will, progress from zero, 1, 2, to 3. In this way, the treating physician can easily keep track of the number of turns that the helical electrode has been rotated into the tissue. FIG. 18S shows dot 362 as it has progressed to the two rotation mark within slot 358.

FIG. 19A shows yet another mechanism 370 for tracking the rotational progress of the drive shaft and helical electrode into the tissue. Mechanism 370 includes a bushing (or inner shaft) 372 having visual counting indicia 374 (including numbers 0, 1, 2, and 3, in this embodiment), Bushing 374 is disposed within an outer tube 378, which can be cooperatively helically threaded with bushing 374 such that the rotational progress of tube 374 is accompanied by a longitudinal progression within tube 378. Mechanism 370 includes a wider shoulder portion 376 which limits the longitudinal and rotational progression of bushing 372 within tube 378. In this embodiment, only a little more than three rotations are allowed by the wider limiting shoulder 376. In some embodiments, shoulder 378 may itself be part of a outer tube which is threadably and rotatably secured about bushing 372, thereby allowing the number of rotations itself to be varied by changing the longitudinal position of shoulder region 376 with respect to bushing 374. Once shoulder 376 contacts the receiving tube 378, the rotation will be limited. FIG. 19S illustrates bushing 352 after it has been rotated about three turns into tube 378 and, presumably, into the tissue target site.

In still another embodiment, an audible clicking mechanism provides audible feedback as the rotation of the drive shaft handle is performed. The number of clicks can thus provide an indication to the treating physician of the progress of the rotation of the helical electrode. In yet another embodiment, a clutch or slip mechanism only transmits the rotation of the drive shaft handle up to a certain number of rotations, and, after that, causes rotation of the drive shaft handle to slip rather than transmit torque down the drive shaft. These mechanisms are but examples of the general mechanisms of providing audio or visual feedback to the treating physician and the general mechanisms of indicating the number of turns and/or limiting the number of rotations that can be performed by the treating physician.

FIG. 20A shows one helical electrode 400 including a distal region 406 and a proximal region 404 having a larger radius of curvature and more pronounced helical angle in the distal region. The proximal inter-turn distance is indicated at 402, where the distal inter-turn distance would be much greater, if a turn was ever completed.

FIG. 20B shows another helical coil 410 having distal region 414 and proximal region 412. The distal region coil turns have an angle indicated at 418 (with respect to an orthogonal plane through the coil center longitudinal axis), which is greater than the angle in the proximal region, indicated at 416.

FIG. 21A is an end view of a terminal mapping electrode 430, having a conductive region 432 and a non-conductive region 434. In various embodiments, the conductive region may describe only 90, 120, or 180 degrees of arc, The smaller arc can allow the physician to more accurately locate an optimal placement site.

FIG. 21B is an end view of a terminal mapping electrode 440, having separate conductive regions 442 separated by insulating or non-conductive regions. In some embodiments, separate conductors allow any or all of the separate conductor regions to be individually accessed from the proximal handle region of the device.

In another embodiment of the invention, sensors, which can be acute monitoring sensors, are disposed near the distal tip of the delivery tube, in addition to or in place of the one or more mapping electrodes. As such sensors may resemble electrodes 432 or 442, a separate drawing in addition to FIGS. 21A and 21B is not required. The types of sensors could include but are not limited to temperature sensors, pressure sensors, oxygen sensors, pH sensors, chemical sensors, and combinations thereof. There could be more than one sensor at the tip depending on the application. One or more of electrodes 442 in FIG. 21B could be sensors, for example, each of the four electrodes 442 could be a different type of sensor. The sensor or sensors could also be used in conjunction with the mapping electrode. The sensors could generate a signal indicative of the property measured and transmit the signal along or through the delivery tube, for example using an electrical conductor or a fiber optic conductor. In some embodiments, a fluorescent probe is disposed near a fiber optic shaft tip, which is used to measure one or more properties near the target tissue.

FIGS. 22A and 22B illustrate another delivery system 450 according to the present invention, including a handle 458, a handle extension 460, a drive shaft handle 452, a drive shaft handle distal bushing 454, a controllably bendable delivery catheter 474, a terminal mapping electrode 472, and a drive shaft handle proximal bushing 455. A distal region slot 476 is formed through the catheter side wall in this embodiment. Slot or aperture 476 can be used in conjunction with an electrode within (e.g. electrode 346 in FIG. 15) for mapping while the terminal electrode is still disposed within the delivery catheter. Some such apertures are shorter or even circular in configuration. A locking button 456 is provided for preventing unwanted advancement of the helical electrode during mapping. In this embodiment, FIG. 22B shows locking button 456 actuating a locking pin 462 to prevent rotation and/or advancement of drive shaft handle 452 within proximal bushing 455.

In use, the lead can be delivered using a catheter. The catheter can be deflectable or steerable and may have a mapping electrode at the distal tip. The lead can be loaded into the catheter, along-side or within the drive shaft. The proximal end or connector of the lead can be secured to the drive shaft in some methods. The distal visualization device (for example, a fiber optic scope or solid state camera) can be placed down the lumen of the drive shaft and through the aperture in the lead head in some methods. The distal visualization device may be an integral part of one of the delivery tubes in other methods, and not require separate advancement or withdrawal. The drive shaft with the distal visualization device and the lead can be passed down the catheter.

The delivery catheter can be placed through a port in the chest wall (for example a thorascopic or sub-xyphoid positioned port). The tip can be placed between the pericardium and the epicardium and advanced to the desired location. The operator can then visualize the location using the scope. The delivery may also be performed, as appropriate, through a mind thoracotomy, a transvenous puncture, or puncturing the right atrial appendage from within to gain access to the heart pericardium.

While one important use of the present invention is in placing epicardial leads, the present invention may be used to place leads using minimally invasive techniques at other target sites. Intramuscular tissue sites are targeted in some methods. Placement of leads for gastric stimulation is another use of the present invention. Applications also include the visualized placement of spinal cord stimulation leads, neurostimulation leads, HIS bundle leads, LV apex leads, sensing leads, and others.

The present invention allows the location of the lead head to be visualized from the proximal region of the lead prior to placement of the lead electrode. In some embodiments, this is accomplished using a fiber optic probe having a shaft with a proximal eyepiece. In other embodiments, the eyepiece is replaced with an electronic camera, for example, a COD camera, for transmitting the image to a larger display or to an even more remote location. In, still other embodiments, the fiber optic probe distal end may be replaced with a small distal camera, for example a solid state camera on a chip. The optical image signal transmission function of the fiber optic shaft may be replaced with an electronic image signal transmission function using an electrical signal conductor or a digital optical signal conductor. The distal end of either such probe may be referred to as an image capturing sensor. The optical fiber or electrical conductor may be referred to as an image transmitting conductor. The image capturing sensor and image transmitting conductor may be part of the delivery tube in some systems.

In some methods the delivery catheter has a conductive distal, region which can be used to test the electrical properties of a potential site prior to fixing the electrode. In one method, the mapping tip is used to pace the heart. In another method, the mapping tip is used to provide electrical stimulation to other tissue, for example, nerve, muscle, or gastric tissue. In still other methods, the mapping tip is used to sense electrical activity from tissue, for example the heart, nerve, muscle, or other tissue. Such test stimulation or sensing may also be accomplished by using the lead electrode extending from the delivery catheter prior to fixing the electrode.

In some devices, the mapping electrode is a terminal ring electrode on the distal tip of the delivery tube. The ring may be masked in some embodiments, being conductive over only part of the ring, to better localize the mapping. In some such devices, only 180, 120, or 90 degrees of arc of the ring are conductive. In some devices, the mapping electrode function may be performed using more than one electrode. In some such devices, the ring is separated into two semi-circular electrodes, three 120 arc degree electrodes, or four 90 arc degree electrodes, with each electrode having its own conductor extending back along the delivery tube to the handle. In some embodiments, the delivery sheath has one or more apertures through the side wall, allowing an electrode within to sense and/or stimulate tissue through the aperture in the side wall.

In a preferred embodiment, the electrode is a helical electrode, and the fixing includes rotating the helical coil into the tissue. In another embodiment, tissue penetration is still accomplished, but with a barbed electrode. While surface, patch type electrode are less preferred, placement of such electrodes may also be accomplished using remote visualization of the target site.

After the distal terminal electrode has been fixed in the tissue, in some embodiment methods, the fiber optic shaft and the drive shaft can be retracted through the delivery tube, over or alongside the lead body. The delivery tube can when be retracted over the lead body.

Various examples of the present invention have been described in the preceding text and in the drawings, which are not necessarily to scale, unless otherwise noted. The scope of the invention is in the claims which follow.

What is claimed is:

1. An implantable medical lead assembly configured for fixing an electrode connected to the lead to tissue in a human body, the lead assembly comprising:
   a) an elongated lead body extending from a proximal lead portion to a distal lead portion, wherein the proximal lead portion is detachably connectable to an implantable medical device and wherein at least the distal lead portion has a first longitudinal, axis and a distal lead portion diameter aligned generally perpendicular to the first longitudinal axis;
   b) an electrical conductor disposed along at least part of the lead body;
   c) a lead head comprising an annular lead head sidewall having a sidewall thickness extending from a sidewall outer surface to a sidewall, inner surface surrounding an aperture in the lead head, the lead head aperture extending along a second longitudinal axis from a proximal lead head end to a distal lead head end providing a tissue contact surface, wherein the distal lead portion is connected to the lead head sidewall at an attachment point so that the first longitudinal axis of the distal lead portion is radially offset from the second longitudinal axis of the lead head aperture; and
   d) an electrode coupled to the lead head, the electrode configured to be fixedly secured to body tissue to conduct electricity from the electrical conductor to the body tissue,
   e) wherein the distal lead portion is movable at the attachment point to the lead head from a constrained position to an unconstrained position,
      i) wherein the distal lead portion diameter is substantially equal to or less than the lead head sidewall thickness so that when in the constrained position, the first longitudinal axis of the distal lead portion is disposed at less than about a 30 degree angle with respect to the second longitudinal axis of the lead head aperture to thereby leave the lead head aperture substantially unobstructed by the distal lead portion, and ii) wherein in the unconstrained position, the distal lead portion lays across the lead head aperture to contact the lead head sidewall opposite the attachment point.

2. The lead assembly of claim 1 further including a drive shaft extending from a proximal drive shaft portion to a distal drive shaft portion, wherein the distal drive shaft portion is releasably attachable to the proximal end of the lead head to thereby provide the lead body and the drive shaft in a side-by-side relationship and wherein the proximal drive shaft portion is manipulatable to impart rotational movement to the lead head to thereby fixedly secure the electrode into body tissue and wherein the drive shaft is further detachable from the lead head connected to the lead with the electrode remaining fixedly secured to the body tissue.

3. The lead assembly of claim 2 wherein the drive shaft has a drive shaft lumen therethrough, and wherein a fiber optic shaft is movable into the drive shaft lumen and into the lead head aperture.

4. The lead assembly of claim 3 further comprising a delivery tube having a delivery tube lumen therethrough, wherein the drive shaft, the lead body, and the fiber optic shaft are movable into and through the delivery tube lumen for at least a part of their respect drive shaft, lead body and fiber optic shaft lengths.

5. The lead assembly of claim 4 wherein the lead body is disposed at about a right angle to the lead head tissue contact surface while unconstrained and not within the delivery tube.

6. The lead assembly of claim 4 wherein the electrode is a helical electrode having an electrode longitudinal axis and wherein the first longitudinal, axis of the distal lead portion is substantially parallel to the electrode longitudinal axis when the distal lead portion attached to the lead head sidewall are in the constrained position in the delivery tube, and wherein the first longitudinal axis of the distal lead portion is substantially parallel with the lead head tissue contact surface when the distal lead portion is removed from the delivery tube and in the unconstrained position.

7. The lead assembly of claim 4 further comprising a handle coupled to the delivery tube, wherein the handle comprises a locking mechanism having a locked position and an unlocked position and wherein rotation of the drive shaft is prevented in the locked position and rotation of the drive shaft is allowed in the unlocked position.

8. The lead assembly of claim 4 wherein the delivery tube includes a steerable distal portion bendable through remote actuation.

9. The lead assembly of claim 2 wherein the lead body is operably coupled to the drive shaft to rotate with and about the first longitudinal axis during manipulation of the drive shaft in a rotational manner.

10. The lead assembly of claim 1 wherein when the electrode is fixedly secured to the body tissue, the second longitudinal axis of the lead head aperture is aligned substantially orthogonally with respect to the lead head tissue contact surface so that a shaft inserted through the lead head aperture while the tissue contact surface is disposed toward the tissue can contact the tissue.

11. The lead assembly of claim 1 wherein the electrode has an electrode central axis and wherein the second longitudinal, axis of the lead head aperture is substantially axially aligned with the electrode central axis.

12. The lead assembly of claim 1 wherein the electrode is a helical electrode.

13. The lead assembly of claim 12 wherein the helical electrode has an interior and the lead head aperture provides access to the helical electrode interior through the lead head.

14. The lead assembly of claim 12 wherein the helical electrode has an electrode longitudinal axis and a plane orthogonal thereto, and wherein the electrode comprises a helically coiled elongated electrode member having coil turns tilted at an angle with respect to the orthogonal plane.

15. The lead assembly of claim 14 wherein the helically coiled elongated electrode member has a coil turn distance between adjacent coil turns with a helical coil distal portion having a coil turn distance that is greater than a helical coil proximal portion coil turn distance.

16. The lead assembly of claim 15 wherein a helical coil distal portion angle is greater than a helical coil proximal portion angle.

17. The lead assembly of claim 1 wherein in the unconstrained position with the distal lead portion laying across the lead head aperture to contact the lead head sidewall opposite the attachment point, the first longitudinal axis of the distal lead portion is disposed at greater than about a 60 degree angle with respect to the second longitudinal axis of the lead head aperture.

18. The lead assembly of claim 17 wherein the lead head is hingedly connected to the distal lead portion at the attachment point.

19. The lead assembly of claim 1 wherein the electrode is a helical electrode having a distal tip and wherein a tip angle changes near the distal tip to point more towards a distal direction than a proximal portion of the electrode adjacent to a proximal electrode end connected to the lead head.

20. The lead assembly of claim 1 further comprising a fiber optic shaft disposed along at least part of the length of the lead body, wherein the fiber optic shaft is movable into the lead head aperture.

21. The lead assembly of claim 1 wherein in the unconstrained position, the distal lead portion substantially obstructs the lead head aperture.

22. An implantable medical lead comprising:
   a) an elongated lead body extending from a proximal lead portion to a distal lead portion, wherein the proximal lead portion is detachably connectable to an implantable medical device and wherein at least the distal lead portion has a first longitudinal axis and a distal lead portion diameter aligned generally perpendicular to the first longitudinal axis;
   b) an electrical conductor disposed along at least part of the lead body;
   c) a lead head comprising an annular lead head sidewall having a sidewall thickness extending from a sidewall outer surface to a sidewall inner surface surrounding an aperture in the lead head, the lead head aperture extending along a second longitudinal axis from a proximal lead head end to a distal lead head end, wherein the distal lead portion is connected to the lead head sidewall at an attachment point so that the first longitudinal axis of the distal lead portion is radially offset from the second longitudinal axis of the lead head aperture; and
   d) an electrode coupled to the distal lead head end, the electrode configured to be fixedly secured to body tissue to conduct electricity from the electrical conductor to the body tissue,
   e) wherein the distal lead portion is movable at the attachment point to the lead head from a constrained position to an unconstrained position, i) wherein the distal lead portion diameter is substantially equal to or less than the lead head sidewall thickness so that when in the constrained position, the first longitudinal axis of the distal portion is disposed at less than about a 30 degree angle with respect to the second longitudinal axis of the lead head aperture to thereby leave the lead head aperture substantially unobstructed by the distal lead portion, and ii) wherein in the unconstrained position, the distal lead portion lays across the lead head aperture to contact the lead head sidewall opposite the attachment point.

* * * * *

UNITED STATES PATENT AND TRADEMARK OFFICE
CERTIFICATE OF CORRECTION

PATENT NO. : 8,868,210 B2  Page 1 of 1
APPLICATION NO. : 14/038984
DATED : October 21, 2014
INVENTOR(S) : John M. Swoyer et al.

It is certified that error appears in the above-identified patent and that said Letters Patent is hereby corrected as shown below:

In the Claims

Column 14, line 49 (Claim 1, line 15) after the word "sidewall" delete the ","

Column 15, line 36 (Claim 6, line 3) after the word "longitudinal" delete the ","

Signed and Sealed this
Tenth Day of March, 2015

Michelle K. Lee
*Deputy Director of the United States Patent and Trademark Office*